(12) United States Patent
Busuek et al.

(10) Patent No.: US 8,901,101 B2
(45) Date of Patent: Dec. 2, 2014

(54) MEMBRANE LYTIC POLY(AMIDO AMINE) POLYMERS FOR THE DELIVERY OF OLIGONUCLEOTIDES

(75) Inventors: Marina Busuek, Center Valley, PA (US); Rubina G. Parmar, Harleysville, PA (US); Michael Steven Poslusney, Nashville, TN (US); Weimin Wang, Churchville, PA (US); J. Michael Williams, Hillsborough, NJ (US)

(73) Assignee: Sirna Therapeutics, Inc., Cambridge, MA (US)

( * ) Notice: Subject to any disclaimer, the term of this patent is extended or adjusted under 35 U.S.C. 154(b) by 0 days.

(21) Appl. No.: 13/993,698

(22) PCT Filed: Dec. 12, 2011

(86) PCT No.: PCT/US2011/064308
§ 371 (c)(1),
(2), (4) Date: Jun. 13, 2013

(87) PCT Pub. No.: WO2012/082574
PCT Pub. Date: Jun. 21, 2012

(65) Prior Publication Data
US 2013/0289207 A1   Oct. 31, 2013

Related U.S. Application Data

(60) Provisional application No. 61/424,216, filed on Dec. 17, 2010.

(51) Int. Cl.
*A61K 48/00* (2006.01)
*A61K 47/48* (2006.01)
*C12N 15/87* (2006.01)
*C08G 73/02* (2006.01)

(52) U.S. Cl.
CPC ..... *A61K 47/48207* (2013.01); *A61K 47/48215* (2013.01); *C12N 15/87* (2013.01); *C08G 73/028* (2013.01)
USPC ............. 514/44 R; 514/44 A; 514/772.4; 514/788; 525/54.2; 528/332; 528/363; 528/367; 528/392; 526/303.1; 526/304; 526/306; 526/307.1; 526/307.3; 536/23.1

(58) Field of Classification Search
CPC ........... A61K 31/7088; A61K 31/7105; A61K 31/711; A61K 31/713; A61K 31/785; A61K 47/34; C08G 73/028; C08L 79/02; C08L 2203/02
USPC .......... 514/44 R, 44 A, 772.4, 788; 525/54.2; 526/303.1, 304, 306, 307.1, 307.3; 536/22.1, 23.1; 528/332, 363, 367, 392
See application file for complete search history.

(56) References Cited

U.S. PATENT DOCUMENTS

| | | |
|---|---|---|
| 6,696,424 B1 | 2/2004 | Wheeler |
| 2009/0130752 A1 * | 5/2009 | Kim et al. .................. 435/320.1 |
| 2009/0220615 A1 * | 9/2009 | Frechet et al. ................ 424/501 |
| 2013/0149783 A1 * | 6/2013 | Yockman et al. ............. 435/440 |

OTHER PUBLICATIONS

Lin, C., et al.; Journal of Controlled Release, 2007, p. 67-75.*
Lin, C., et al.; Bioconjugate Chemistry, 2007, p. 138-145.*
Lin, C., et al.; Journal of Controlled Release, 2006, p. 130-137.*
Malgesini, B et al., Macromolecular Bioscience, vol. 3, (2003), pp. 59-66, "Poly(amido-amine)s Carrying Primary Amino Groups as Side Substituents".

* cited by examiner

*Primary Examiner* — Robert Jones, Jr.
(74) *Attorney, Agent, or Firm* — Jeffrey N. Townes; LeClair Ryan

(57) ABSTRACT

The present invention provides membrane lytic poly(amido amine) polymers, polyconjugates, compositions and methods for the delivery of oligonucleotides for therapeutic purposes.

9 Claims, 7 Drawing Sheets

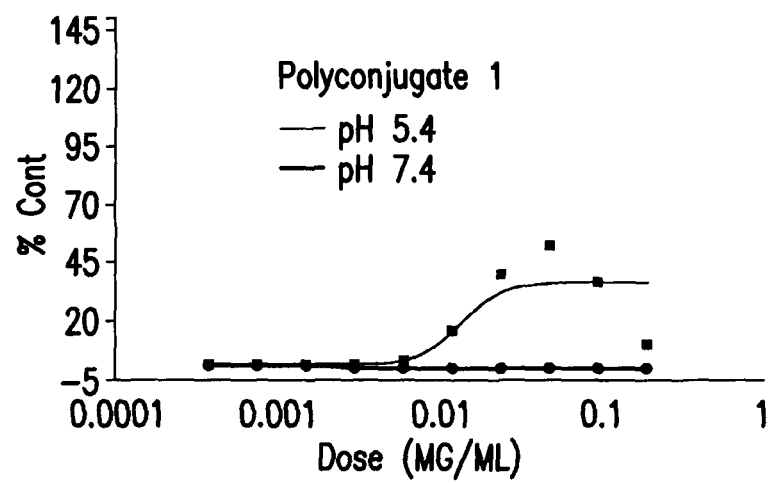
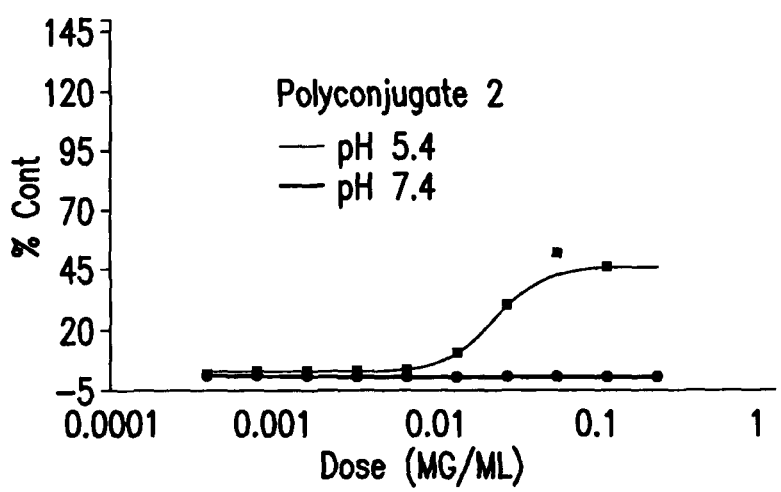
FIG. 1

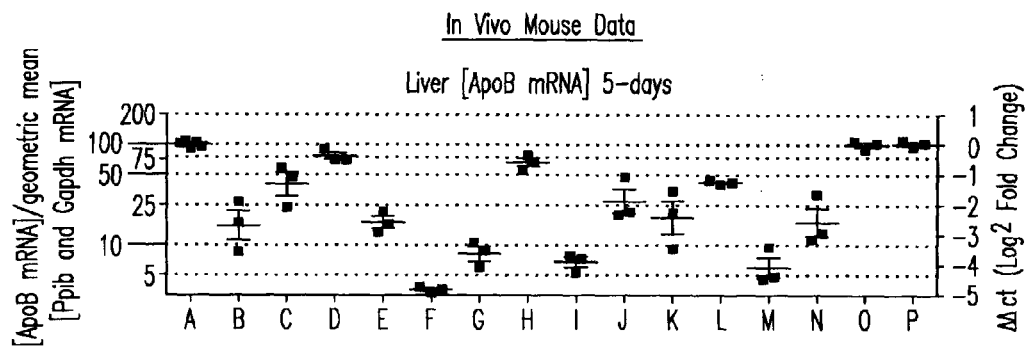

| ID | Polyconjugate | siRNA | Polymer:siRNA Ratio | siRNA Dose (mpk) | Polymer:siRNA conjugation efficiency (%) | Masking efficiency of unpurified polyconjugates(%) |
|---|---|---|---|---|---|---|
| A | Buffer | | | | | |
| B | Polyconjugate 1 | Active siRNA 1 | 4:1 | 6 | 93 | — |
| C | Polyconjugate 1 | Active siRNA 1 | 4:1 | 3 | 94 | — |
| D | Polyconjugate 1 | Active siRNA 1 | 4:1 | 1 | 93 | 61 |
| E | Polyconjugate 1 | Active siRNA 1 | 8:1 | 3 | 94 | 77 |
| F | Polyconjugate 2 | Active siRNA 1 | 6:1 | 6 | 93 | 52 |
| G | Polyconjugate 2 | Active siRNA 1 | 6:1 | 3 | 94 | 61 |
| H | Polyconjugate 2 | Active siRNA 1 | 6:1 | 1 | 93 | 81 |
| I | Polyconjugate 2 | Active siRNA 1 | 4:1 | 6 | 93 | 55 |
| J | Polyconjugate 2 | Active siRNA 1 | 4:1 | 3 | 93 | 59 |
| K | Polyconjugate 1 | Active siRNA 2 | 4:1 | 6 | 94 | 54 |
| L | Polyconjugate 1 | Active siRNA 2 | 4:1 | 3 | 93 | 57 |
| M | Polyconjugate 2 | Active siRNA 2 | 6:1 | 6 | 94 | 92 |
| N | Polyconjugate 2 | Active siRNA 2 | 6:1 | 3 | 94 | 92 |
| O | Polyconjugate 2 | Control siRNA 1 | 6:1 | 6 | 93 | — |
| P | Polyconjugate 1 | Control siRNA 1 | 4:1 | 6 | 94 | 46 |

Active siRNA 1 = Zimmerman Apo B
Active siRNA 2 = Sci 10 Apo B
Control siRNA = Low Hex 9

FIG.2

Active siRNA 1 = Zimmerman Apo B
Active siRNA 2 = Sci 10 Apo B

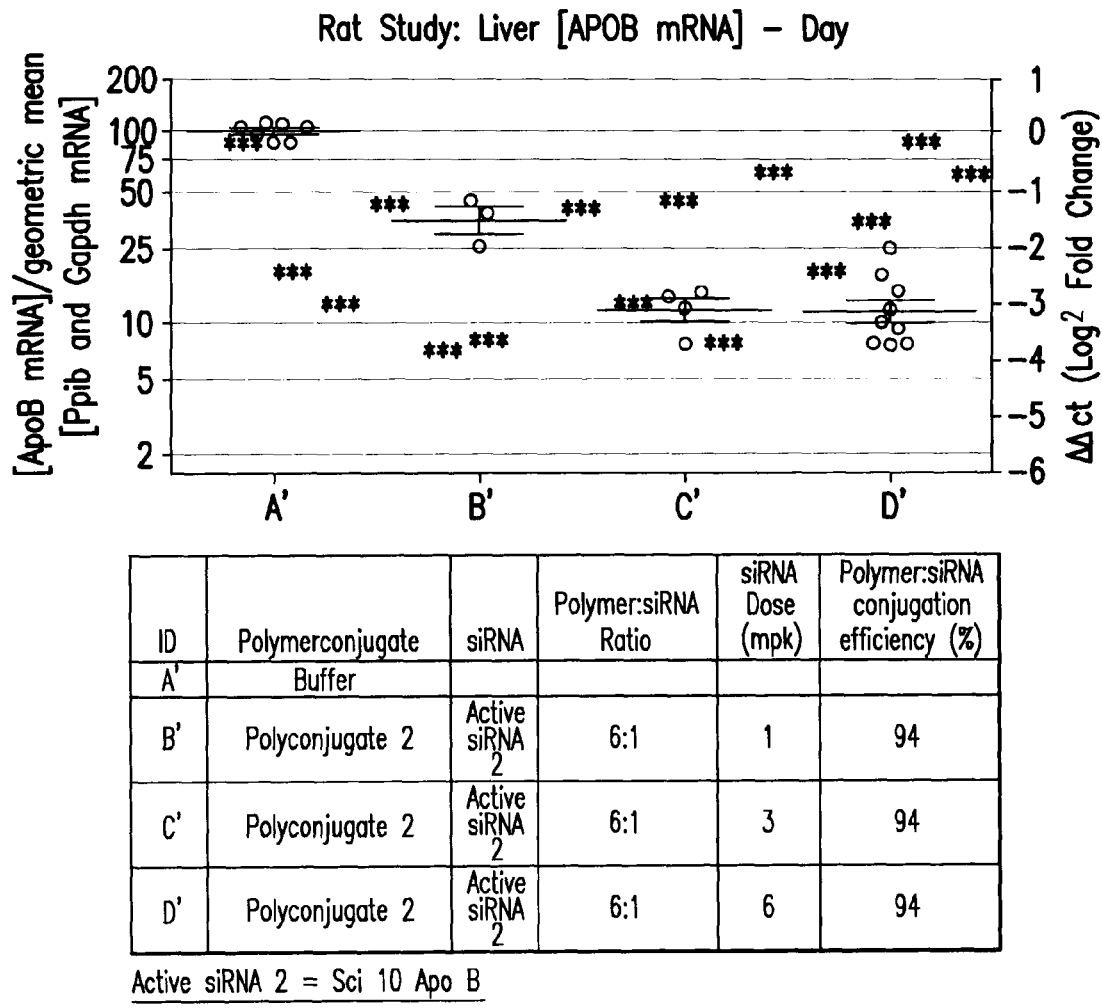
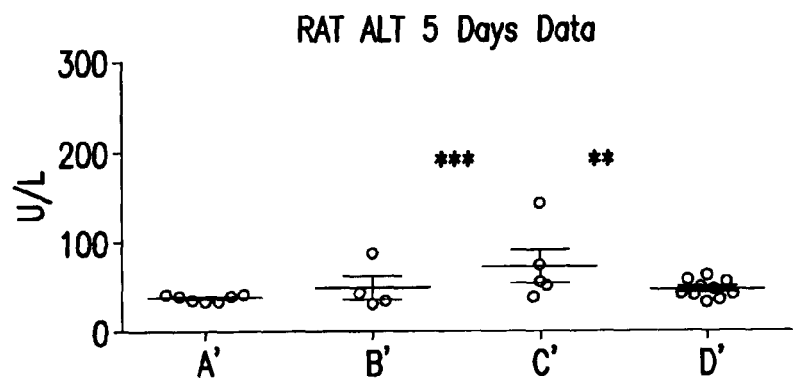
FIG.4

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(4)
<223> OTHER INFORMATION: 2' O-methyl
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (5)..(6)
<223> OTHER INFORMATION: 2' fluoro
<220> FEATURE:
<221> NAME/KEY: misc_feature
<222> LOCATION: (7)..(7)
<223> OTHER INFORMATION: 2' O-methyl
<220> FEATURE:
<221> NAME/KEY: misc_feature
<222> LOCATION: (8)..(9)
<223> OTHER INFORMATION: 2' fluoro
<220> FEATURE:
<221> NAME/KEY: misc_feature
<222> LOCATION: (10)..(14)
<223> OTHER INFORMATION: 2' O-methyl
<220> FEATURE:
<221> NAME/KEY: misc_feature
<222> LOCATION: (15)..(18)
<223> OTHER INFORMATION: 2' fluoro
<220> FEATURE:
<221> NAME/KEY: misc_feature
<222> LOCATION: (19)..(19)
<223> OTHER INFORMATION: 2' O-methyl
<220> FEATURE:
<221> NAME/KEY: misc_feature
<222> LOCATION: (20)..(21)
<223> OTHER INFORMATION: 2' deoxy
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted deoxy abasic

<400> SEQUENCE: 1
cuuuaacaau uccugaaaut t                                             21

<210> SEQ ID NO 2
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: phosphorotioate linkage
<220> FEATURE:
<221> NAME/KEY: misc_feature
<222> LOCATION: (5)..(5)
<223> OTHER INFORMATION: 2' O-methyl
<220> FEATURE:
<221> NAME/KEY: misc_feature
<222> LOCATION: (6)..(10)
<223> OTHER INFORMATION: 2' fluoro
<220> FEATURE:
<221> NAME/KEY: misc_feature
<222> LOCATION: (11)..(12)
<223> OTHER INFORMATION: 2' O-methyl
<220> FEATURE:
```

```
<221> NAME/KEY: misc_feature
<222> LOCATION: (13)..(14)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(19)
<223> OTHER INFORMATION: 2' fluoro
<220> FEATURE:
<221> NAME/KEY: misc_feature
<222> LOCATION: (20)..(21)
<223> OTHER INFORMATION: 2' O-methyl
<220> FEATURE:
<221> NAME/KEY: misc_feature
<222> LOCATION: (20)..(21)
<223> OTHER INFORMATION: phosphorothioate linkage

<400> SEQUENCE: 2
auuucaggaa uuguuaaagu u                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: amino linker
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(2)
<223> OTHER INFORMATION: 2' fluoro
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (3)..(4)
<223> OTHER INFORMATION: 2' deoxy
<220> FEATURE:
<221> NAME/KEY: misc_feature
<222> LOCATION: (5)..(6)
<223> OTHER INFORMATION: 2' fluoro
<220> FEATURE:
<221> NAME/KEY: misc_feature
<222> LOCATION: (7)..(9)
<223> OTHER INFORMATION: 2' deoxy
<220> FEATURE:
<221> NAME/KEY: misc_feature
<222> LOCATION: (10)..(10)
<223> OTHER INFORMATION: 2' fluoro
<220> FEATURE:
<221> NAME/KEY: misc_feature
<222> LOCATION: (11)..(11)
<223> OTHER INFORMATION: 2' deoxy
<220> FEATURE:
<221> NAME/KEY: misc_feature
<222> LOCATION: (12)..(12)
<223> OTHER INFORMATION: 2' fluoro
<220> FEATURE:
<221> NAME/KEY: misc_feature
<222> LOCATION: (13)..(13)
<223> OTHER INFORMATION: 2' deoxy
<220> FEATURE:
<221> NAME/KEY: misc_feature
<222> LOCATION: (14)..(15)
```

```
<223> OTHER INFORMATION: 2' fluoro
<220> FEATURE:
<221> NAME/KEY: misc_feature
<222> LOCATION: (16)..(17)
<223> OTHER INFORMATION: 2' deoxy
<220> FEATURE:
<221> NAME/KEY: misc_feature
<222> LOCATION: (18)..(18)
<223> OTHER INFORMATION: 2' fluoro
<220> FEATURE:
<221> NAME/KEY: misc_feature
<222> LOCATION: (19)..(21)
<223> OTHER INFORMATION: 2' deoxy
<220> FEATURE:
<221> NAME/KEY: misc_feature
<222> LOCATION: (21)..(21)
<223> OTHER INFORMATION: inverted deoxy abasic

<400> SEQUENCE: 3
cuagcuggac acgucgauau t                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2' fluoro
<220> FEATURE:
<221> NAME/KEY: misc_feature
<222> LOCATION: (5)..(6)
<223> OTHER INFORMATION: 2' O-methyl
<220> FEATURE:
<221> NAME/KEY: misc_feature
<222> LOCATION: (7)..(7)
<223> OTHER INFORMATION: 2' fluoro
<220> FEATURE:
<221> NAME/KEY: misc_feature
<222> LOCATION: (8)..(8)
<223> OTHER INFORMATION: 2' O-methyl
<220> FEATURE:
<221> NAME/KEY: misc_feature
<222> LOCATION: (9)..(9)
<223> OTHER INFORMATION: 2' fluoro
<220> FEATURE:
<221> NAME/KEY: misc_feature
<222> LOCATION: (10)..(10)
<223> OTHER INFORMATION: 2' O-methyl
<220> FEATURE:
<221> NAME/KEY: misc_feature
<222> LOCATION: (11)..(13)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(17)
<223> OTHER INFORMATION: 2' fluoro
```

```
<220> FEATURE:
<221> NAME/KEY: misc_feature
<222> LOCATION: (18)..(21)
<223> OTHER INFORMATION: 2' O-methyl
<220> FEATURE:
<221> NAME/KEY: misc_feature
<222> LOCATION: (20)..(21)
<223> OTHER INFORMATION: phosphorothioate linkage

<400> SEQUENCE: 4
uaucgacgug uccagcuagu u                                              21
```

MEMBRANE LYTIC POLY(AMIDO AMINE) POLYMERS FOR THE DELIVERY OF OLIGONUCLEOTIDES

REFERENCE TO SEQUENCE LISTING SUBMITTED ELECTRONICALLY

The sequence listing of the present application is being submitted electronically via EFS-Web as an ASCII formatted sequence listing with a file name "MRLMIS00043USPCT-SEQTXT-17MAY2013.txt", creation date of May 17, 2013 and a size of 4.52 KB. This sequence listing submitted via EFS-Web is part of the specification and is herein incorporated by reference in its entirety.

BACKGROUND OF THE INVENTION

Oligonucleotides conjugated to polymers are known. Further, the delivery of oligonucleotides conjugated to polymers (polyconjugates) for therapeutic purposes is also known. See WO2000/34343; WO2008/022309; and Rozema et al. PNAS (2008) 104, 32: 12982-12987.

Poly(amido amine) polymers are known. Z. Khayat et al. International Journal of Pharmaceutics (2006) 317:175-186; P. Ferruti et al. Macromol. Rapid Commun. (2002) 23:332-355; and Ka-Wai Wan et al. Biomacromolecules (2004) 5:1102-1109.

Polyconjugates have numerous toxicities associated with it as an oligonucleotide delivery vehicle. It is thus an object of the invention to provide polyconjugates that are biodegradable. Further, it is also an object of the invention to provide polyconjugates designed with components to increase liver uptake. Further, it is also an object of the instant invention to provide polyconjugates designed with components that facilitate oligonucleotide escape from the endosome. Herein, we disclose and describe novel membrane lytic poly(amido amine) polymers and polyconjugates useful for the delivery of oligonucleotides for therapeutic purposes.

SUMMARY OF THE INVENTION

The present invention provides membrane lytic poly(amido amine) polymers, polyconjugates, compositions and methods for the delivery of oligonucleotides for therapeutic purposes.

BRIEF DESCRIPTION OF THE FIGURES

FIG. 1. RBC Hemolysis Data of Polyconjugates

FIG. 2. Liver Apo B mRNA-Mice

FIG. 4. Liver Apo mRNA and ALT-Rats

DETAILED DESCRIPTION OF THE INVENTION

Figure 3:
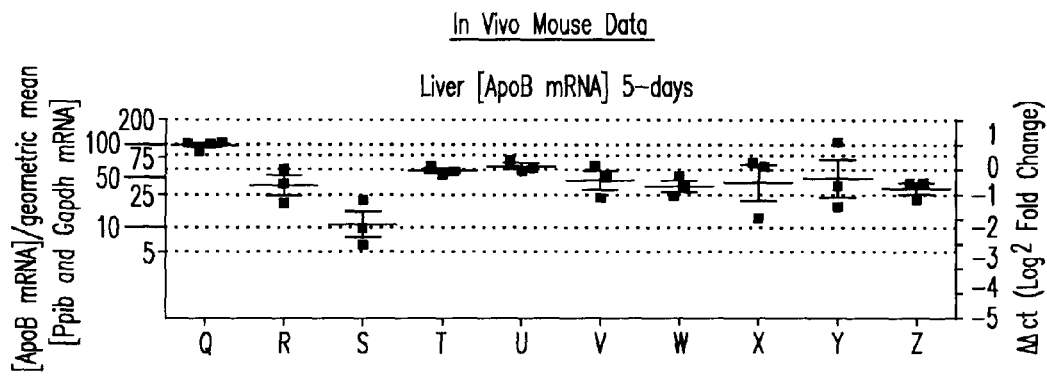
FIG. 3. Liver Apo B mRNA-Mice
Figure 5:
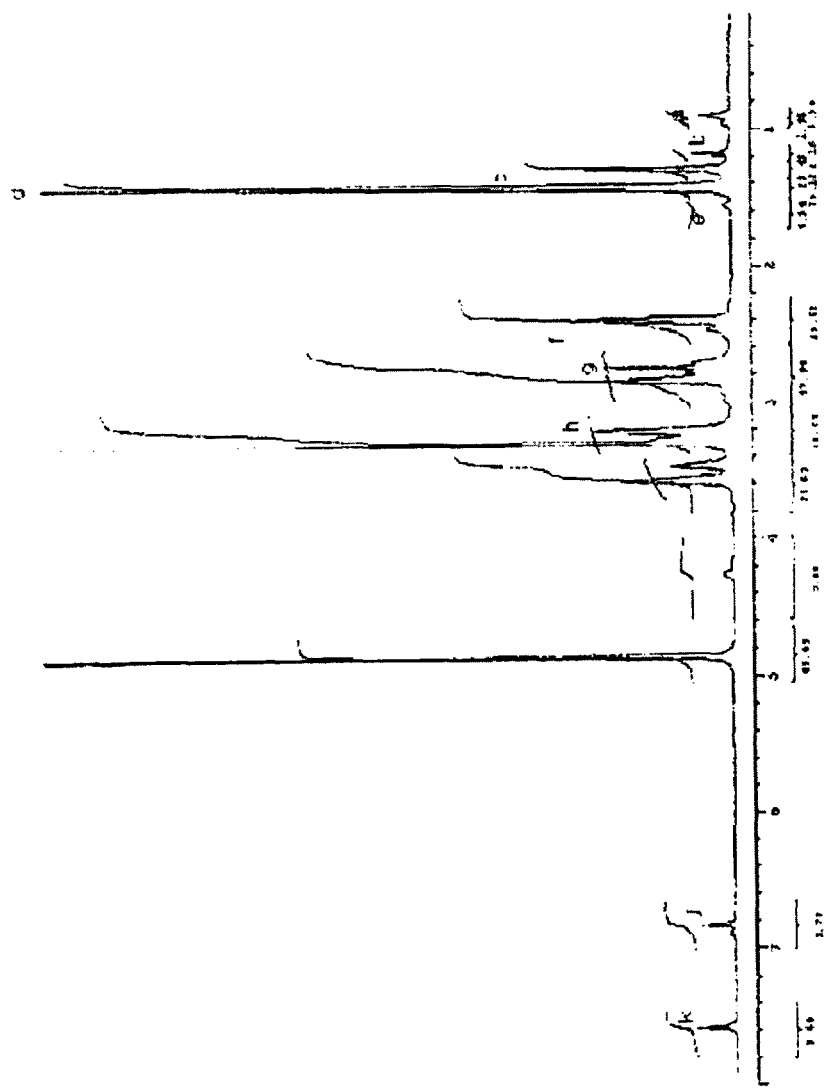
FIG. 5. NMR spectra for the synthesized poly (amido amine) "PPA" polymers recorded on varian spectrometer operating at 500 MHz.
Figure 6:
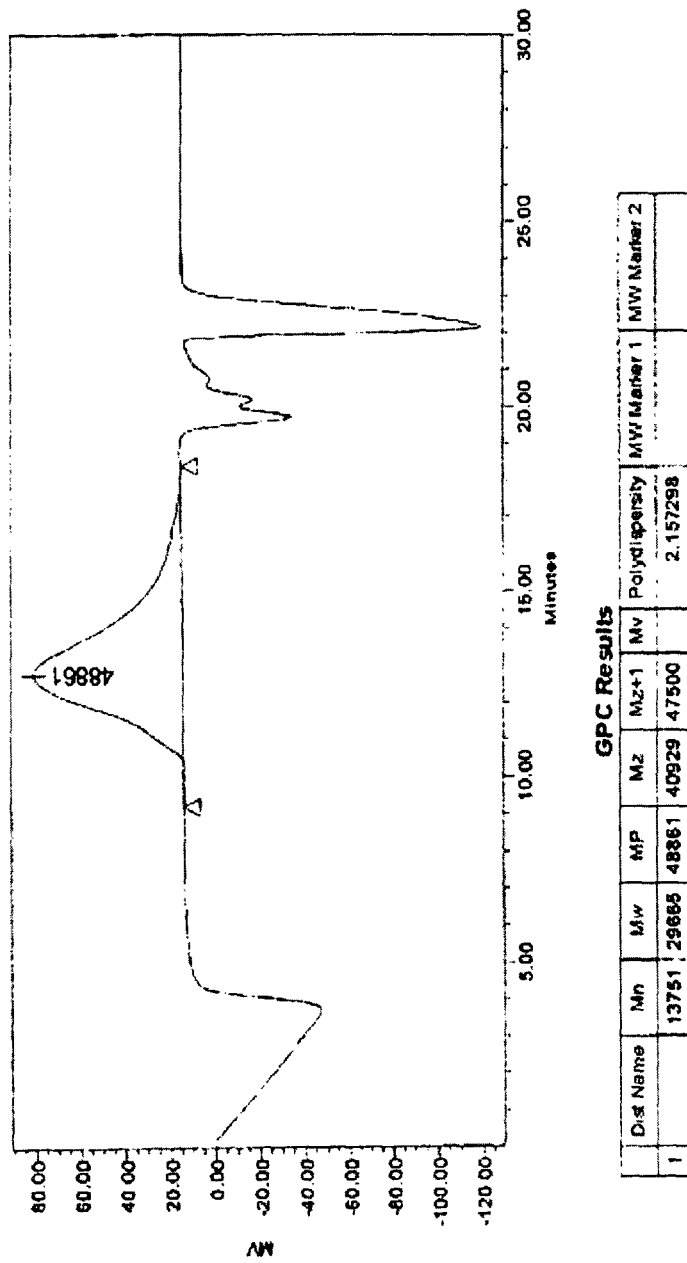
FIG. 6. The molecular weight and polydispersity (Mw/Mn) of the synthesized poly (amido amine) "PPA" polymers determined by GPC.
Figure 7:
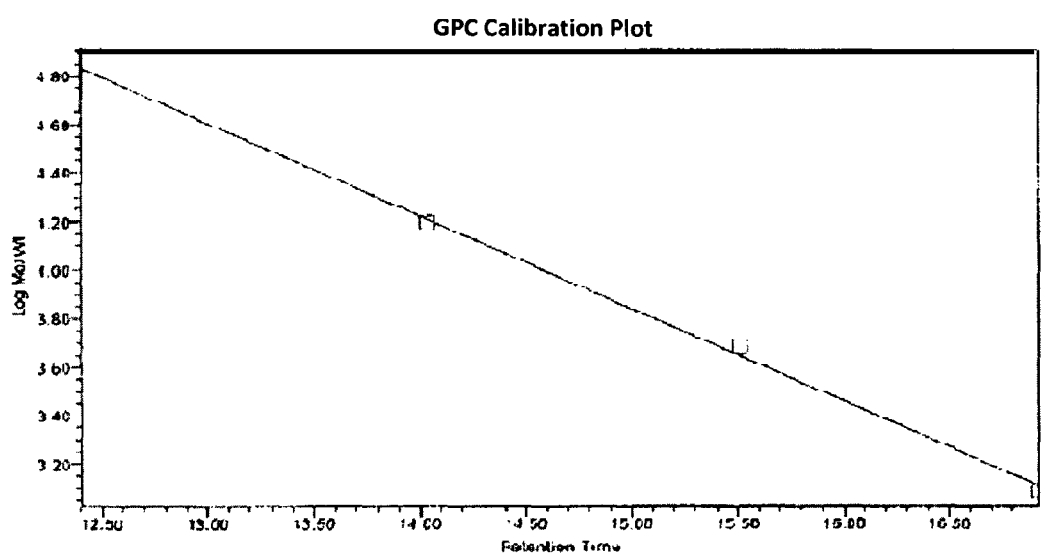
FIG. 7. GPC calibration plot and GPC calibration table for the synthesized poly (amido amine) "PPA" polymers.

An embodiment of the instant invention is a polymer comprising Formula Z:

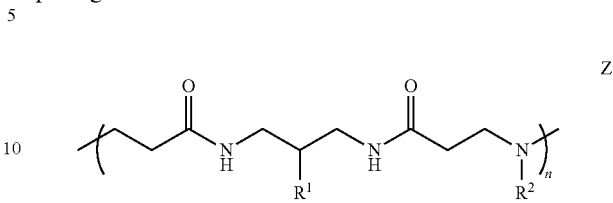

wherein:
n is 2 to 250;
$R^1$ is independently selected from a primary, secondary, tertiary and quaternary amine; and
$R^2$ is independently selected from a primary, secondary, tertiary and quaternary amine, a heterocyclic amine, and a lipophilic group; or a stereoisomer thereof.

Another embodiment of the instant invention is a polymer comprising Formula Z':

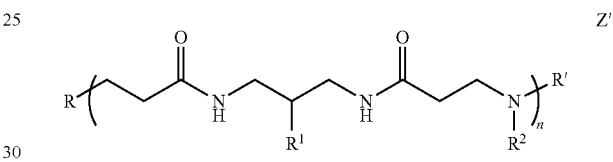

wherein:
n is 2 to 250;
R is a capped end group selected from a primary and secondary amine;
R' is hydrogen or methylene;
$R^1$ is independently selected from a primary, secondary, tertiary and quaternary amine; and
$R^2$ is independently selected from a primary, secondary, tertiary and quaternary amine, a heterocyclic amine, and a lipophilic group;
or a stereoisomer thereof.

In another embodiment of the instant invention is a polymer comprising Formula Z', wherein:
n is 2 to 250;
R is $C_4H_9NH$;
R' is hydrogen;
$R^1$ is aminoethoxy; and
$R^2$ is independently selected from dodecyl, 2-(1H-imidazol-4-yl)ethyl and 2-(2-aminoethoxy)ethyl;
or a stereoisomer thereof.

In another embodiment of the instant invention is a polymer conjugate composition comprising a polymer of Formula Z or Z', a linker and an oligonucleotide.

In another embodiment of the instant invention is the polymer conjugate composition above further comprising a masking agent.

In another embodiment of the instant invention is the polymer conjugate composition above further comprising a targeting ligand.

In another embodiment of the instant invention is the polymer conjugate composition above further comprising a masking agent and a targeting ligand.

In another embodiment of the instant invention is a polymer conjugate composition made by the 1) synthesis of an activated polymer comprising Formula Z or Z'; 2) synthesis of an activated oligonucleotide; and 3) conjugation of the activated polymer with the activated oligonucleotide; optionally including the addition of a masking agent and/or a targeting ligand.

In another embodiment of the instant invention is a method of treating a disease in a patient by administering a polymer conjugate composition of the instant invention.

Definitions

"Amine (primary, secondary, tertiary or quaternary)" means organic compounds and functional groups that contain a basic nitrogen atom with a lone pair. Amines are derivatives of ammonia, wherein one or more hydrogen atoms have been replaced by a substituent such as an alkyl or aryl group.

"Capped end group(s)" means the terminal end group(s) of polymers that inhibit the ability of the polymer to continue polymeriazation.

"Heterocyclic amine" means an organic compound containing at least one atom of carbon and at least one atom on nitrogen within a ring structure. These structures may comprise either simple aromatic rings or non-aromatic rings.

"Disease" means a disorder or incorrectly functioning organ, part, structure, or system of the body resulting from the effect of genetic or developmental errors, infection, poisons, nutritional deficiency or imbalance, toxicity, or unfavorable environmental factors; illness; sickness; ailment. An example of a disease is cancer.

"Lipophilic group" means groups having affinity for lipids. Lipophilic substances interact within themselves and with other substances through the dispersion force and they have little to no capacity to form hydrogen bonds.

"Linker" means a chemical moiety that physically conjugates the oligonucleotide with a polymer comprising Formula Z or Z'.

"Masking agent" means a molecule which, when linked to a polymer, shields, inhibits or inactivates one or more properties (biophysical or biochemical characteristics) of the polymer. Masking agents may be attached covalentely to targeting ligands or polyethylene glycol. See WO2008/022309 for a more detailed description of masking agents.

"Oligonucleotide" means deoxyribonucleic acid (DNA) and ribonucleic acid (RNA) and combinations of DNA, RNA and other natural and synthetic nucleotides, including protein nucleic acid (PNA). DNA maybe in form of cDNA, in vitro polymerized DNA, plasmid DNA, parts of a plasmid DNA, genetic material derived from a virus, linear DNA, vectors (P1, PAC, BAC, YAC, and artificial chromosomes), expression vectors, expression cassettes, chimeric sequences, recombinant DNA, chromosomal DNA, anti-sense DNA, or derivatives of these groups. RNA may be in the form of messengerRNA (mRNA), in vitro polymerized RNA, recombinant RNA, transfer RNA (tRNA), small nuclear RNA (snRNA), ribosomal RNA (rRNA), chimeric sequences, antisense RNA, interfering RNA, small interfering RNA (siRNA), microRNA (miRNA), ribozymes, external guide sequences, small non-messenger RNAs (snmRNA), untranslatedRNA (utRNA), snoRNAs (24-mers, modified snmRNA that act by an anti-sense mechanism), tiny non-coding RNAs (tncRNAs), small hairpin RNA (shRNA), or derivatives of these groups. In addition, DNA and RNA may be single, double, triple, or quadruple stranded. Double, triple, and quadruple stranded polynucleotide may contain both RNA and DNA or other combinations of natural and/or synthetic nucleic acids. Oligonucleotides can be chemically modified. The use of chemically modified oligonucleotides can improve various properties of the oligonucleotides including, but not limited to: resistance to nuclease degradation in vivo, cellular uptake, activity, and sequence-specific hybridization. Non-limiting examples of such chemical modifications include: phosphorothioate internucleotide linkages, LNA, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. These chemical modifications, when used in various oligonucleotide constructs, are shown to preserve oligonucleotide activity in cells while at the same time, dramatically increasing the serum stability of these compounds. Chemically modified siRNA can also minimize the possibility of activating interferon activity in humans. See WO2008/022309 for a more detailed description of oligonucleotides.

"Polyethylene glycols" (PEGs) are non-toxic and non-immunogenic polyether compounds. They can be added to media and attached to surfaces and conjugated to molecules without interfering with cellular functions or target immunogenicities. When attached to biomolecules PEGs decrease aggregation and increase aqueous solubility.

"Polymer" means a molecule built up by repetitive bonding together of smaller units called monomers. A polymer can be linear, branched, network, star, comb, or ladder type. A polymer can be a homopolymer in which a single monomer is used or a polymer can be copolymer in which two or more different monomers are used. Copolymers may by alternating, random (statistical), gradient, block and graft (comb). The monomers in random copolymers have no definite order or arrangement along any given chain. The general compositions of such polymers are reflective of the ratio of input monomers. However, the exact ratio of one monomer to another may differ between chains. The distribution of monomers may also differ along the length of a single polymer. Also, the chemical properties of a monomer may affect its rate of incorporation into a random copolymer and its distribution within the polymer. Thus, while the ratio of monomers in a random polymer is dependent on the input ratio of monomer, the input ratio may not match exactly the ratio of incorporated monomers. See WO2008/022309 for a more detailed description of polymers.

"Patient" means a mammal, typically a human, in need of treatment for a disease.

"Purification step" means a process by which a desired compound is separated from a mixture of other compounds.

"Tangential Flow Filtration (TFF)" means a rapid and efficient method for filtration and separation of solutions containing large molecules, biomolecules, or particles such as viruses, bacteria or cellular material. It is a process whereby product flow (feed) is directed tangentially along the surface of a membrane with most of the solution circulated back to the feed tank. The rapid flow of feed solution across the membrane acts to 'sweep' the surface, reducing concentration polarization (product concentration at the membrane surface). It also prevents build-up of foulants that can plug the pores at the membrane surface. The rapid cross flow creates a pressure drop, which forces some of the feed solution and dissolved molecules that are smaller than the pores in the membrane, through the membrane filter. The solution that passes through the membrane is referred to as filtrate or permeate. Molecules or particles larger than the membrane pores are retained in the feed solution and effectively concentrated.

"Targeting ligand", also referred to as "targeting agent", means an agent that can deliver a polymer or polyconjugate to target cells or tissues, or specific cells types. Targeting ligands enhance the association of molecules with a target cell. Thus, targeting ligands can enhance the pharmacokinetic or biodistribution properties of a polyconjugate to which they are attached to improve cellular distribution and cellular uptake of the conjugate. See WO2008/022309 for a more detailed description of targeting ligands.

In an embodiment of Formula Z or Z', n is 2 to 250.
In another embodiment of Formula Z or Z', n is 2 to 225.
In another embodiment of Formula Z or Z', n is 2 to 200.
In another embodiment of Formula Z or Z', n is 2 to 175.
In another embodiment of Formula Z or Z', n is 2 to 150.
In another embodiment of Formula Z or Z', n is 2 to 125.
In another embodiment of Formula Z or Z', n is 2 to 100.
In another embodiment of Formula Z or Z', n is 2 to 75.
In another embodiment of Formula Z or Z', n is 2 to 50.
In another embodiment of Formula Z or Z', n is 2 to 25.
In an embodiment of Formula Z or Z', n is 5 to 250.
In another embodiment of Formula Z or Z', n is 5 to 225.
In another embodiment of Formula Z or Z', n is 5 to 200.
In another embodiment of Formula Z or Z', n is 5 to 175.
In another embodiment of Formula Z or Z', n is 5 to 150.
In another embodiment of Formula Z or Z', n is 5 to 125.
In another embodiment of Formula Z or Z', n is 5 to 100.
In another embodiment of Formula Z or Z', n is 5 to 75.
In another embodiment of Formula Z or Z', n is 5 to 50.
In another embodiment of Formula Z or Z', n is 5 to 25.
In another embodiment of Formula Z or Z', n is 10 to 60.
In another embodiment of Formula Z or Z', n is 15 to 55.
In another embodiment of Formula Z or Z', n is 20 to 50.
In another embodiment of Formula Z or Z', n is 25 to 45.
In another embodiment of Formula Z or Z', n is 30 to 40.
In an embodiment R is $C_4H_{10}N$.
In an embodiment R' is hydrogen.
In an embodiment, $R^1$ is independently selected from a primary, secondary, tertiary and quaternary amine.
In another embodiment, $R^1$ is independently selected from aminoethoxy, 2-(2-aminoethoxy)ethyl, 2-[2-2-aminoethoxy)ethoxy]ethyl, 2-[2-(2-aminoethoxy)ethoxy]ethyl, 3-amino-2-hydroxypropyl, 2-aminoethyl, 4-aminobutyl, 6-aminohexyl, 8-aminooctyl and 10-aminodecyl.
In another embodiment, $R^1$ is aminoethoxy.
In an embodiment, $R^2$ is independently selected from a primary, secondary, tertiary and quaternary amine, a heterocyclic amine, and a lipophilic group.
In another embodiment, $R^2$ is independently selected from 2-(2-aminoethoxy)ethyl, 2-[2-(2-aminoethoxy)ethoxy]ethyl, 2-[2-(2-aminoethoxy)ethoxy]ethyl, 3-amino-2-hydroxypropyl, 2-aminoethyl, 4-aminobutyl, 6-aminohexyl, 8-aminooctyl, 10-aminodecyl, 2-(1H-imidazol-4-yl)ethyl, 2-(4-methyl-1H-imidazol-5-yl)ethyl, 2-(1-Ethyl-1H-imidazol-4-yl)-ethyl, 2-(5-Methyl-3H-imidazol-4-yl)-ethyl, 2-(2-isopropyl-1-methyl-1H-imidazol-4-yl)ethyl, 2-(1-butyl-1H-imidazol-4-yl)ethyl, 2-(1-hexyl-1H-imidazol-4-yl)ethyl, 2-(1-octyl-1H-imidazol-4-yl)ethyl, 2-(1-dodecyl-1H-imidazol-4-yl)ethyl, 2-pyridin-4-yl ethyl, 2-(2,6-dimethylpyridin-4-yl)ethyl, 2-pyridin-2-yl ethyl, 2-pyridin-3-yl ethyl, 2-piperazin-1-yl ethyl, [4-(2-ethyl)piperidin-1-yl]methanol and 2-morpholin-4-ylethyl.
In another embodiment, $R^2$ is independently selected from 2-(1H-imidazol-4-yl)ethyl, 2-(4-methyl-1H-imidazol-5-yl)ethyl, 2-(1-Ethyl-1H-imidazol-4-yl)-ethyl, 2-(5-Methyl-3H-imidazol-4-yl)-ethyl, 2-(2-isopropyl-1-methyl-1H-imidazol-4-yl)ethyl, 2-(1-butyl-1H-imidazol-4-yl)ethyl, 2-(1-hexyl-1H-imidazol-4-yl)ethyl, 2-(1-octyl-1H-imidazol-4-yl)ethyl, 2-(1-dodecyl-1H-imidazol-4-yl)ethyl, 2-pyridin-4-yl ethyl, 2-(2,6-dimethylpyridin-4-yl)ethyl, 2-pyridin-2-yl ethyl, 2-pyridin-3-yl ethyl, 2-piperazin-1-yl ethyl, [4-(2-ethyl)piperidin-1-yl]methanol and 2-morpholin-4-ylethyl.

In another embodiment, $R^2$ is independently selected from a lipophilic group which is selected from an alkyl group, an alkenyl group and an alkynyl group, all of which may be branched or cyclic or acyclic or aromatic.

In an embodiment, a linker is the chemical moiety which is made by the conjugation of a derivative of SMPT (4-succinimidyloxycarbonyl-(-methyl-(-[2-pyridyldithio]toluene) and/or a derivative of SATA (N-Succinimidyl-S-acetylthioacetate).

In an embodiment, a masking agent is selected from a maleic anhydride derivative.

In an embodiment, a masking agent is selected from a disubstituted maleic anhydride derivative.

In an embodiment, a targeting ligand is selected from compounds with affinity to cell surface molecules, cell receptor ligands, and antibodies, antibody fragments, and antibody mimics with affinity to cell surface molecules.

In another embodiment, a targeting ligand is selected from carbohydrates, glycans, saccharides (including, but not limited to: galactose, galactose derivatives, mannose, and mannose derivatives), vitamins, folate, biotin, aptamers, and peptides (including, but not limited to: RGD-containing peptides, insulin, EGF, and transferrin).

In another embodiment, a targeting ligand is selected from N-acetylgalactosamine (NAG), mannose and glucose.

In another embodiment, a targeting ligand is N-acetylgalactosamine (NAG).

In an embodiment, an oligonucleotide is selected from siRNA, miRNA and antisense. In another embodiment, an oligonucleotide is an siRNA.

In an embodiment, the polymers of Formula Z or Z' are copolymers.

In an embodiment, the polymers of Formula Z or Z' are copolymers which are random.

In an embodiment, the polymers of Formula Z or Z' are copolymers which are gradient.

In an embodiment, the polymers of Formula Z or Z' are copolymers which are block.

Formulation

The polyconjugate, also known as "polymer conjugate" (composition of the polymer comprising Formula Z or Z' and an oligonucleotide) is formed by covalently linking the oligonucleotide to the polymer. Conjugation of the oligonucleotide to the polymer can be performed in the presence of an excess of polymer. Because the oligonucleotide and the polymer may be of opposite charge during conjugation, the presence of excess polymer can reduce or eliminate aggregation of the polyconjugate. Excess polymer can be removed from the polyconjugate prior to administration of the polyconjugate to a patient. Alternatively, excess polymer can be co-administered with the polyconjugate to the patient.

Similarly, the polymer can be conjugated to a masking agent in the presence of an excess of polymer or masking agent. Because the oligonucleotide and the polymer may be of opposite charge during conjugation, the presence of excess polymer can reduce or eliminate aggregation of the polyconjugate. Excess polymer can be removed from the polyconjugate prior to administration of the polyconjugate to a patient. Alternatively, excess polymer can be co-administered with the polyconjugate to the patient. The polymer can be modified prior to or subsequent to conjugation of the oligonucleotide to the polymer.

Similarly, the polymer can be conjugated to a targeting ligand in the presence of an excess of polymer or targeting ligand. Because the oligonucleotide and the polymer may be of opposite charge during conjugation, the presence of excess polymer can reduce or eliminate aggregation of the polyconjugate. Excess polymer can be removed from the polyconjugate prior to administration of the polyconjugate to a patient. Alternatively, excess polymer can be co-administered with the polyconjugate to the patient. The polymer can be modified prior to or subsequent to conjugation of the oligonucleotide to the polymer.

Similarly, the polymer can be conjugated to a PEG in the presence of an excess of polymer. Because the oligonucleotide and the polymer may be of opposite charge during conjugation, the presence of excess polymer can reduce or eliminate aggregation of the polyconjugate. Excess polymer can be removed from the polyconjugate prior to administration of the polyconjugate to a patient. Alternatively, excess polymer can be co-administered with the polyconjugate to the patient. The polymer can be modified prior to or subsequent to conjugation of the oligonucleotide to the polymer.

Parenteral routes of administration include intravascular (intravenous, interarterial), intramuscular, intraparenchymal, intradermal, subdermal, subcutaneous, intratumor, intraperitoneal, intrathecal, subdural, epidural, and intralymphatic injections that use a syringe and a needle or catheter. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, bile ducts, and ducts of the salivary or other exocrine glands. The intravascular route includes delivery through the blood vessels such as an artery or a vein. The blood circulatory system provides systemic spread of the pharmaceutical. An administration route involving the mucosal membranes is meant to include nasal, bronchial, inhalation into the lungs, or via the eyes. Intraparenchymal includes direct injection into a tissue such as liver, lung, heart, muscle (skeletal muscle or diaphragm), spleen, pancreas, brain (including intraventricular), spinal cord, ganglion, lymph nodes, adipose tissues, thyroid tissue, adrenal glands, kidneys, prostate, and tumors. Transdermal routes of administration have been affected by patches and iontophoresis. Other epithelial routes include oral, nasal, respiratory, rectum, and vaginal routes of administration.

The polyconjugates can be injected in a pharmaceutically acceptable carrier solution. Pharmaceutically acceptable refers to those properties and/or substances which are acceptable to the patient from a pharmacological/toxicological point of view. The phrase pharmaceutically acceptable refers to molecular entities, compositions, and properties that are physiologically tolerable and do not typically produce an allergic or other untoward or toxic reaction when administered to a patient. Preferably, as used herein, the term pharmaceutically acceptable means approved by a regulatory agency of the Federal or a state government or listed in the U.S. Pharmacopeia or other generally recognized pharmacopeia for use in animals, and more particularly in humans.

Utility

The polyconjugates (compositions of a polymer comprising Formula Z or Z' and an oligonucleotide) of the instant invention may be used for research purposes or to produce a change in a cell that can be therapeutic. The use of polyconjugates for therapeutic purposes is known. See WO2000/34343; WO2008/022309; and Rozema et al. PNAS (2008) 104, 32: 12982-12987.

EXAMPLES

Examples and schemes provided are intended to assist in a further understanding of the invention. Particular materials employed, species and conditions are intended to be further illustrative of the invention and not limitative of the reasonable scope thereof.

Monomer Synthesis

Novel tert-butyl (2-{[1,3-bis(prop-2-enoylamino)propan-2-yl]oxy}ethyl)carbamate (8) was synthesized to increase the amine density of polymer. The monomer was synthesized in seven steps.

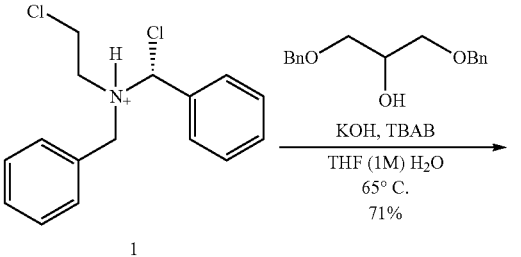

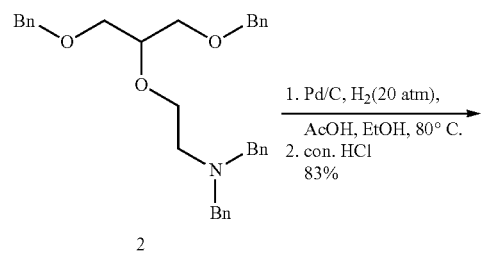

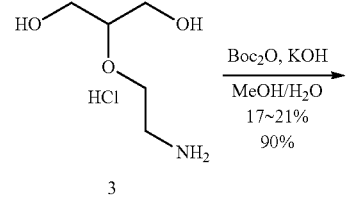

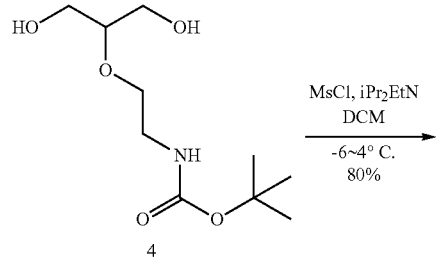

-continued

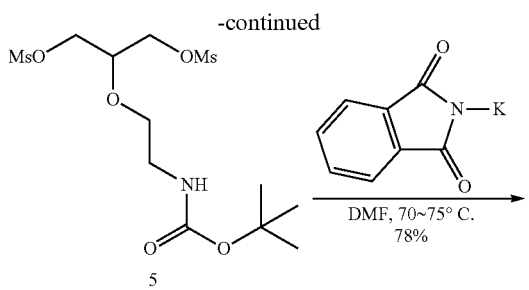

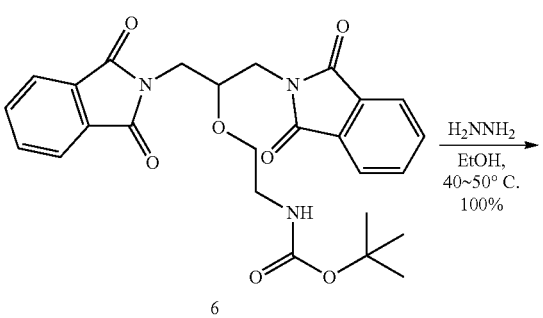

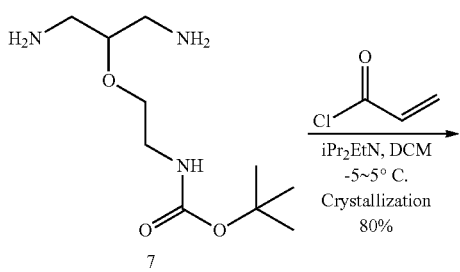

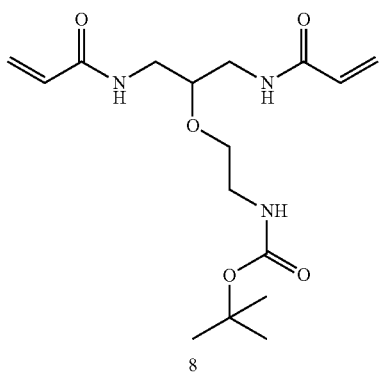

Step 1

A 20-L 4-neck round-bottom flask was flushed with N₂. Then charged a solution of 1,3-bis(benzyloxy)propan-2-ol (2632 g, 9.7 mol, 1.2 eq) in tetrahydrofuran (8400 mL, 3.2 v), N,N-dibenzyl-2-chloroethanaminium chloride (2422 g, 8.2 mol, 1.0 eq), tetrabutylammonium bromide (1020 g, 3.2 mol, 0.4 eq) and a solution of potassium hydroxide (2290 g, 40.9 mol, 5.0 eq) in water (8400 mL, 3.2 v). The resulting solution was stirred overnight at 65~70° C. The reaction progress was monitored with LCMS. After the reaction was finished, the system was cooled to 20~30° C. and then extracted with dichloromethane (2×4000 mL). The combined organic layer was washed with HCl (1M, 2×10 L). Adjusted the organic layer to pH 8 with saturated aq. sodium bicarbonate. The separated organic layer was dried and concentrated under vacuum. The residue was applied onto a silica gel column and eluted with ethyl acetate/petroleum ether (1:100). This resulted in 2888 g (71%) of N,N-dibenzyl-2-(1,3-bis(benzyloxy)propan-2-yloxy)ethanamine as a yellow oil.

Step 2

Charged a solution of N,N-dibenzyl-2-(1,3-bis(benzyloxy)propan-2-yloxy)ethanamine (2000 g, 4.0 mol, 1.0 eq) in EtOH (10000 mL, 5.0 v), Pd/C (10%, 400 g, 20% wt,) and acetic acid (970 g, 16.2 mol, 4.0 eq) to a 20 L pressure reactor. The resulting mixture was stirred for 10 hours at 80° C. under hydrogen (20 atm). The reaction progress was monitored with NMR. The reaction mixture was cooled to 20~30° C. and filtered. HCl (36%, 500 ml, 6.0 mol, 1.5 eq) was added to the filtrate, stirred for 10 minutes and concentrated under vacuum to give 572 g (83.4%) of 2-(2-aminoethoxy)propane-1,3-diol hydrochloride as an oil. H-NMR of 3 (300 MHz, D₂O, ppm): 3.79 (2H, q), 3.60 (2H, m), 3.50 (3H, m), 3.15 (2H, q).

Step 3

A 5-L 4-neck round-bottom flask was flushed with N₂. Then charged a solution of 2-(2-aminoethoxy)propane-1,3-diol (97.2 g, 0.7 mol, 1.0 eq) in methanol (1798 mL, 18.5 v), di-tert-butyl dicarbonate (314.4 g, 1.4 mol, 2.0 eq) and a solution of potassium (88.9 g, 1.6 mol, 2.2 eq) in water (1798 mL, 18.5 v). The resulting solution was stirred for 3.5 h at 17~21° C. in a water bath. The resulting mixture was washed with petroleum ether (1400.0 mL+1200.0 ml) and concentrated under vacuum. The residual solution was extracted with dichloromethane (6×500 mL). The combined organic layer was dried over anhydrous sodium sulfate and concentrated under vacuum to give 79.1 g (59.4%) of tert-butyl 2-(1,3-dihydroxypropan-2-yloxy)ethylcarbamate as a light yellow oil.

H-NMR of 4 (300 MHz, CDCl₃, ppm): 3.74 (6H, m), 3.51 (1H, m), 3.35 (2H, m), 1.47 (9H, s).

Step 4

A 20-L 4-neck round-bottom flask was flushed with N₂, then charged a solution of tert-butyl 2-(1,3-dihydroxypropan-2-yloxy)ethylcarbamate (418 g, 1.8 mol, 1.0 eq) in dichloromethane (9000 mL, 21.5 v) and N,N-diisopropylethylamine (574 g, 4.4 mol, 2.5 eq). This is followed by dropwise addition of methanesulfonyl chloride (509 g, 4.4 mol, 2.5 eq) with stirring at −6-0° C. over 1 hour. The resulting mixture was stirred for 4 h at −6~4° C., then washed with water (3×4000 mL). The organic layer was separated, dried over anhydrous sodium sulfate and concentrated under vacuum. The residue was applied onto a silica gel column and eluted with petroleum ether/EtOAc (1:1) to give 740 g (101.0%) of 2-(2-(tert-butoxycarbonylamino)ethoxy) propane-1,3-diyl dimethanesulfonate as a yellow oil.

H-NMR of 5 (300 MHz, CDCl₃, ppm): 5.05 (1H, s, w), 4.24 (4H, m), 3.81 (1H, m), 3.63 (2H, m), 3.24 (2H, m), 3.02 (6H, s), 1.37 (9H, s).

Step 5

A 20 L 4-neck round-bottom flask was flushed with N₂. Then charged a solution of 2-(2-(tert-butoxycarbonylamino) ethoxy) propane-1,3-diyl-dimethanesulfonate (929 g, 2.37 mol, 1.0 eq) in N,N-dimethylformamide (9300 mL) and potassium phthalimide (2194 g, 11.85 mol, 5.0 eq). The resulting mixture was stirred for 18 hours at 70~75° C. in an oil bath. The reaction progress was monitored with LCMS. The reaction mixture was cooled to 20~30° C., then added icy water (28 L) with stirring. The mixture was stirred for 30 minutes, and then filtered. The filter cake was dried under vacuum at 60° C. to give 919 g (78.5%) tert-butyl 2-(1,3-bis (1,3-dioxoisoindolin-2-yl)propane-2-yloxy)ethylcarbamate as an off-white solid.

LCMS of 6 (ES, m/z): 393.8 [M-Boc]⁺

Step 6

A 20 L 4-neck round-bottom flask was flushed with $N_2$. Then charged a solution of tert-butyl 2-(1,3-bis(1,3-dioxoisoindolin-2-yl)propan-2-yloxy) ethylcarbamate (919 g, 1.9 mol, 1.0 eq) in ethanol (12000 mL, 13.0 v), followed by dropwise addition of hydrazine hydrate (602 g, 12.0 mol, 6.3 eq) with stirring at 40-45° C. over 30 min. The resulting mixture was stirred for 7 hours at 40-45° C. in an oil bath. The reaction progress was monitored with LCMS. The reaction mixture was cooled to 20~30° C. and filtered. The filtrate was concentrated under vacuum to give 424.0 g (97.5%) of tert-butyl 2-(1,3-diaminopropan-2-yloxy) ethylcarbamate as a brown oil.

LCMS of 7 (ES, m/z): 234 [M+H]⁺

H-NMR of 7 (300 MHz, CDCl$_3$, ppm): 5.39 (1H, s, w), 3.60 (2H, q), 3.26 (3H, m), 2.79 (4H, m), 1.43 (9H, s), 1.39 (4H, s)

Step 7

A 5 L 4-neck round-bottom flask was flushed with $N_2$ and kept from light. Then charged a solution of tert-butyl 2-(1,3-tert-butyl2-(1,3-diaminopropan-2-yloxy)ethylcarbamate (300.0 g, 1.3 mol, 1.0 eq) in dichloromethane (3000 mL, 10.0 v) and N-ethyl-N-isopropylpropan-2-amine (332.3 g, 2.6 mol, 2.0 eq), followed by dropwise addition of acryloyl chloride (232.7 g, 2.6 mol, 2.0 eq) with stirring at <3° C. over 150 min. The resulting mixture was stirred for 90 min at 20-24° C. in a water bath. The reaction was monitored with LCMS. The resulting mixture was washed with water (1 L). The organic layer was dried over anhydrous sodium sulfate and concentrated under vacuum. Heptane (6000 ml) was added dropwise with stirring to the residue over 20 minutes, then cooled to 0° C. and stirred for 30 minutes. The solid was collected and washed with hepatane (2×200 mL) to give 218.0 g (48.0%) of tert-butyl 2-(1,3-diacrylamidopropan-2-yloxy)ethylcarbamate as an off-white solid.

LCMS of 8 (ES, m/z): 341.9[M⁺].

H-NMR of 8 (300 MHz, CDCl$_3$, ppm): 6.93 (2H, s, w), 6.25 (4H, m), 5.68 (2H, dd), 3.65 (5H, m), 3.30 (4H, m), 1.46 (9H, s).

General Polymer Synthesis (Scheme 1)

The monomers were weighed and brought up in 30% ethanol solution in water. The reaction mixture was stirred at 55° C. in dark for 5 days under nitrogen atmosphere. After 5 days, polymerization was quenched by adding 20 mol % excess of amine to consume any unreacted acrylate. After that, polymer was precipitated with diethylether and dried. Polymers with Boc-protected oligoamines were deprotected by TFA. The crude polymer was precipitated again in diethylether. The polymer was further purified by dialysis.

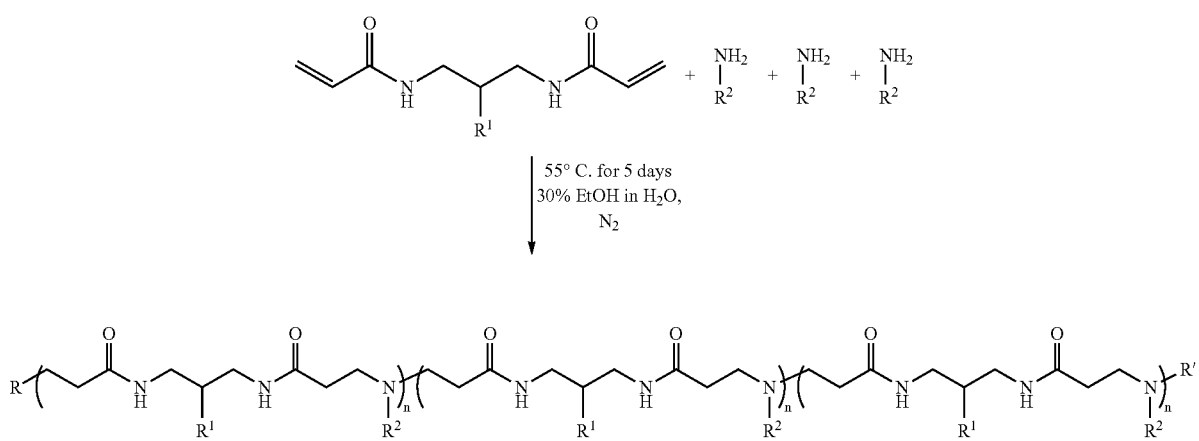

Polymer Synthesis (Scheme 2)

Poly (amido amine) "PAA" polymers were synthesized by polyaddition of primary amines to tert-butyl (2-{[1,3-bis (prop-2-enoylamino)propan-2-yl]oxy}ethyl)carbamate.

In a typical experiment, 8 (1 equiv: 0.585 mmol, 200 mg), tert-butyl [2-(2-aminoethoxy)ethyl]carbamate (0.4 equiv: 0.234 mmol, 47.8 mg), histamine (0.3 equiv: 0.175 mmol, 19.5 mg) and dodecylamine (0.3 equiv: 0.175 mmol, 32.57 mg) were added to a reaction flask. The solvent mixture (30% ethanol in water 1.2 ml; 0.5 M) was added to the reaction flask and the reaction mixture was degassed. Polymerization was carried out in dark at 55° C. under nitrogen atmosphere. The reaction mixture became homogeneous in less than 15 minutes at 55° C. The reaction was allowed to proceed for 5 days. Subsequently, 10-20 mol % of butylamine in EtOH was added to the reaction mixture to consume any unreacted acrylamide groups. The resulting mixture was continued heating overnight (15-20 h) at 65° C. under $N_2$. The reaction mixture was cooled to room temperature and polymer solution was precipitated in 100 ml diethyl ether, centrifuged, decanted, and the residue was flushed with $N_2$. The deprotection of Boc-amine was carried out by dissolving protected polymer in 2 ml of TFA/TIS (triisopropylsilane)/H$_2$O 95/2.5/2.5 solution for 30-60 min at ice bath temperature. The reaction mixture was allowed to warm up to room temperature. The crude polymer was precipitated out again in 100 ml diethyl ether, centrifuged, decanted, and the residue was flushed with $N_2$. The residue was dissolved in 10 ml DI water and the pH was adjusted to pH 7 with 1N NaOH solution. The polymer solution was then transferred in to 2K dialysis bag and dialyzed with Milli-Q water for 24-48 h and then lyophilized.

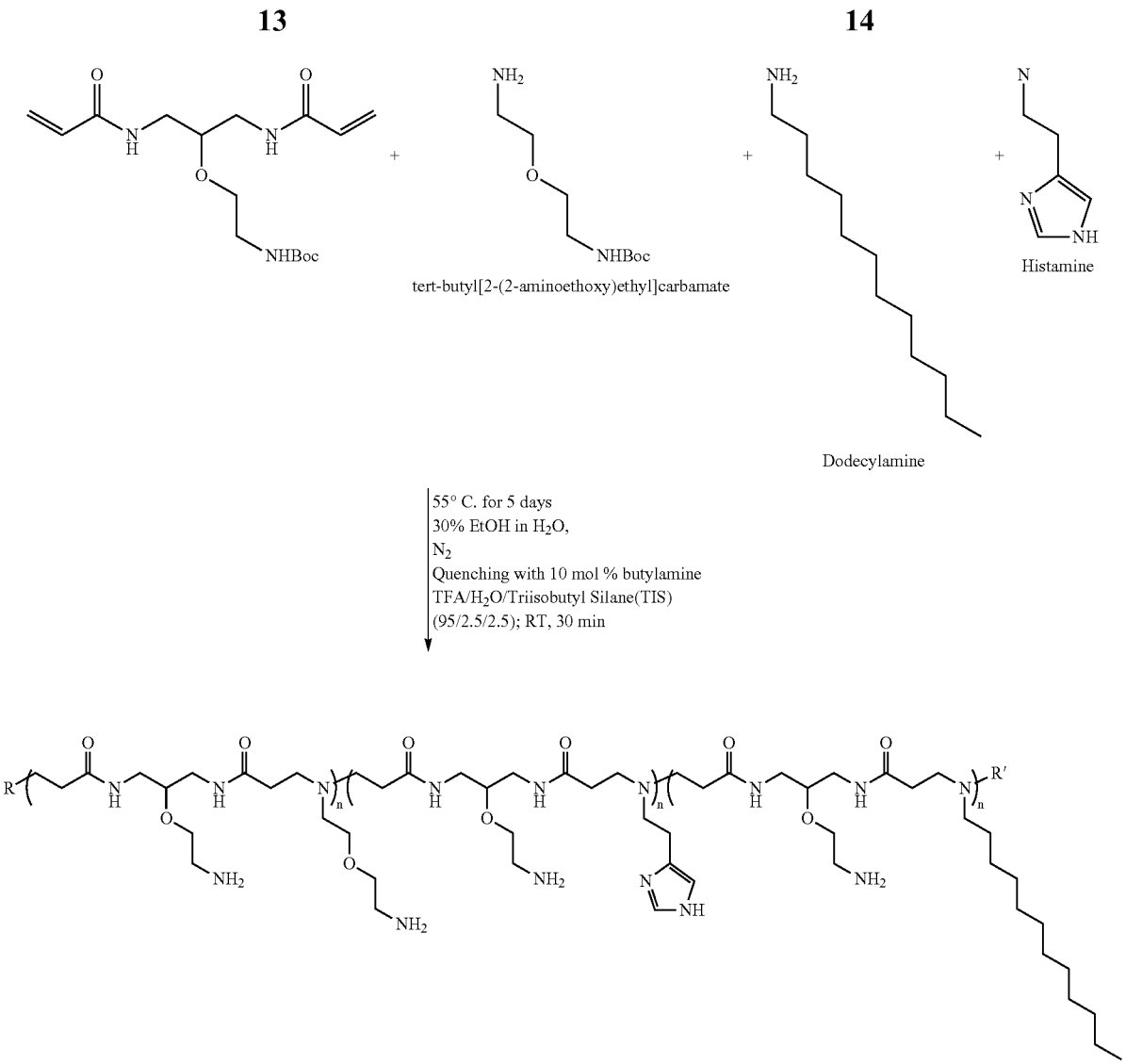

wherein the polymer is random or block and wherein n is independently 0 to 60; R is $C_4H_{10}N$; and R' is hydrogen.

1H and 13C NMR spectra were recorded on varian spectrometer operating at 500 MHz. 1H NMR spectra were in full accordance with the expected structures. No signals were present in the region between 5 and 7 ppm, corresponding to the acrylamide group, indicating that these polymers have capped end groups. Feed ratios of different monomers in the polymers were confirmed by NMR. All NMR spectra were taken in deuterated methanol.

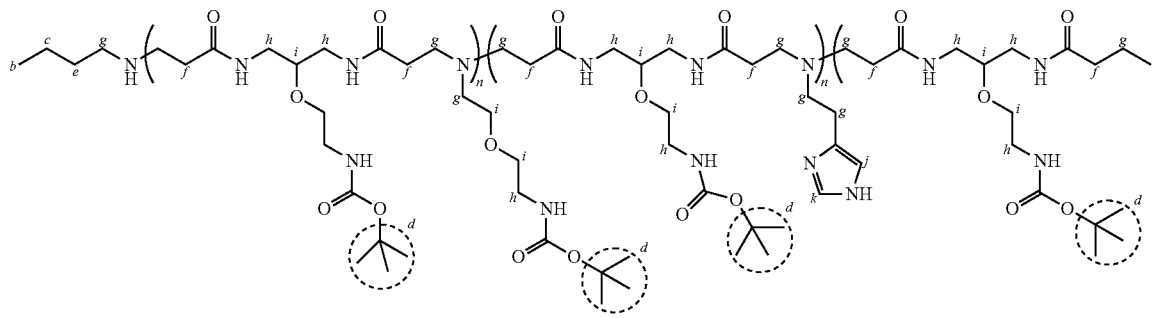

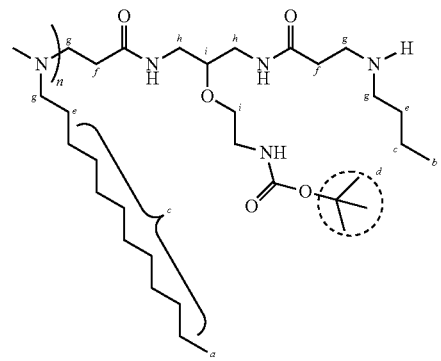

The molecular weight and polydispersity (Mw/Mn) of the synthesized polymers were determined by GPC relative to polystyrene standards (Sigma-Aldrich) using a Waters 2695, Waters 2414 RI detector and TSK-GEL Alpha-3000 column. Polymers have Mn between 5 K to 25 K with PDI=1.3-2.8 .

Polystyrene Standards (Sigma-Aldrich)

The following polymers were prepared according to the General Reaction Scheme and Schemes above.

Polymers

Polymers of the instant invention include:

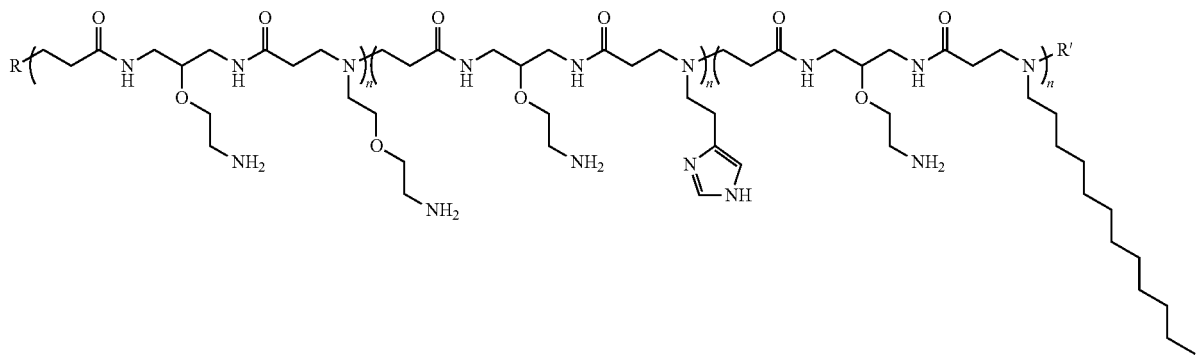

wherein the polymer is random or block and wherein n is independently 0 to 60; R is $C_4H_{10}N$; and R' is hydrogen.

Table 1 demonstrates specific random or block polymers. In Table 1, aminoethoxy is always designated as 100, which means that aminoethoxy is present in each repeating unit of the polymer. 2-(2-aminoethoxy)ethyl-,2-(1H-imidazol-4-yl) ethyl-, and dodecyl-containing repeating units are randomly distributed and incorporated in the identified % ratios, wherein the ratios are +/−5%.

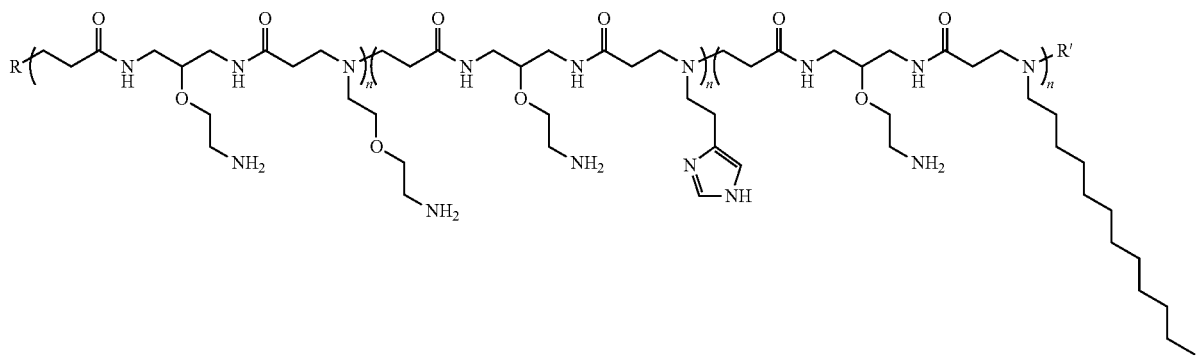

TABLE 1

| aminoethoxy | 2-(2-aminoethoxy)ethyl | 2-(1H-imidazol-4-yl)ethyl | dodecyl |
|---|---|---|---|
| 100 | 30 | 50 | 20 |
| 100 | 40 | 30 | 30 |
| 100 | 30 | 20 | 50 |
| 100 | 0 | 20 | 80 |
| 100 | 70 | 0 | 30 |
| 100 | 20 | 80 | 0 |
| 100 | 40 | 60 | 0 |
| 100 | 50 | 0 | 50 |
| 100 | 50 | 20 | 30 |
| 100 | 50 | 30 | 20 |
| 100 | 60 | 40 | 0 |
| 100 | 60 | 20 | 20 |
| 100 | 60 | 0 | 40 |
| 100 | 70 | 0 | 30 |
| 100 | 70 | 10 | 20 |
| 100 | 70 | 20 | 10 |
| 100 | 80 | 20 | 0 |
| 100 | 80 | 10 | 10 |
| 100 | 80 | 0 | 20 |
| 100 | 90 | 10 | 0 |
| 100 | 90 | 0 | 10 |
| 100 | 100 | 0 | 0 |

General Polymer Conjugation (Scheme 3)

The polymers comprising Formula Z or Z' and the examples shown above were synthesized for use in the following conjugation steps to ultimately create the polyconjugates of the instant invention. The polymers comprising Formula Z or Z' and the examples disclosed are useful in the preparation of polyconjugates which are, in turn, useful for the delivery of oligonucleotides, specifically the delivery of siRNA. Other methods for the synthesis of polyconjugates are described in WO2008/022309.

Activation of Polymer and Oligonucleotide (Functionalization)

Amines on the polymers were functionalized, with the activated group, to allow attachment of the oligonucleotide to the polymer. Also, the oligonucleotide was modified to react with activiated group on the polymer.

Polymer-Oligonucleotide Conjugation

Activated groups on the polymer react with modified oligonucleotide to form polymer-oligonucleotide conjugate.

Free RNA duplex as well as free RNA duplex-dimer was determined by aqueous SEC using a GE Heathsciences Superdex 75HR 10/300 column. The mobile phase was composed of 100 mM Tris with 2M NaCl, pH 8.4. Total RNA (both free and bound) was determined by using Inductively Coupled Plasma (ICP) spectroscopy. Since the RNA is the only phosphorus containing species in the formulations, determining the total phosphorus content can be used to directly determine the total RNA concentration. Once the free RNA (duplex and duplex-dimer) and total RNA is determined, the amount of RNA conjugated to the polymer can be calculated (i.e. conjugation efficiency).

Masking of Polymer Conjugate

Polymer siRNA conjugate was masked with carboxy dimethylmaleic anhydride of N-acetylgalactosamine (CDM-NAG) and carboxy dimethylmaleic anhydride of polyethylene glycol (CDM-PEG).

Total concentrations of CDM-NAG and CDM-PEG were determined using reverse-phase HPLC with mobile phases of 0.1% TFA in water and 0.1% TFA in 70/30 methanol:acetonitrile. Rapid demasking of the polymer after injection onto the column allows quantitation of CDMs with the polymer removed using a C18 guard column to prevent chromatographic interference. Free (i.e. unbound) CDM-NAG and CDM-PEG is analyzed by first filtering through a 10K centrifuge filter followed by analysis using the same reverse-phase HPLC method. Masking Efficiency can be calculated by first calculating the bound RNA, CDM-NAG and CDM-PEG. The polymer molecular weight in combination with the total amines available for conjugation is then used with the bound ligands to calculate masking efficiency.

Purification of Polymer Conjugate (Optional)

Tangential flow filtration (TFF) process was used to purify masked polymer conjugate formulations of un-incorporated components and to exchange buffer to pharmaceutically acceptable formulation vehicle. The TFF filter material was made of either modified polyethersulfone (PES) or regenerated cellulose. The selection of molecular weight cutoff for these membranes was done with efficiency of purification and retention of polymer conjugate in mind. The processing parameters, including but not limited to feed pressure, retentate pressure, crossflow rate and filtrate flux were set to allow reproducibility from batch to batch and linear scaling of the process. Using the difiltration mode of TFF, the reaction impurities were filtered out into the permeate while the retained polymer conjugate underwent a buffer exchange. The purification was done at refrigerated conditions. After TFF, the final product was concentrated to 0.4-2.0 mg/ml of siRNA and sterile filtered using a 0.2 μm PES syringe filter and stored at −20° C. until use.

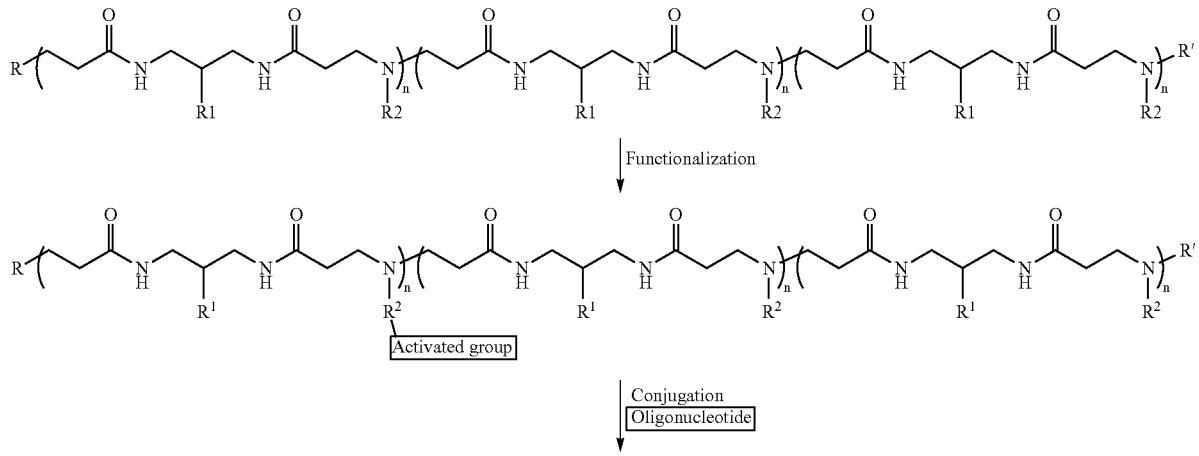

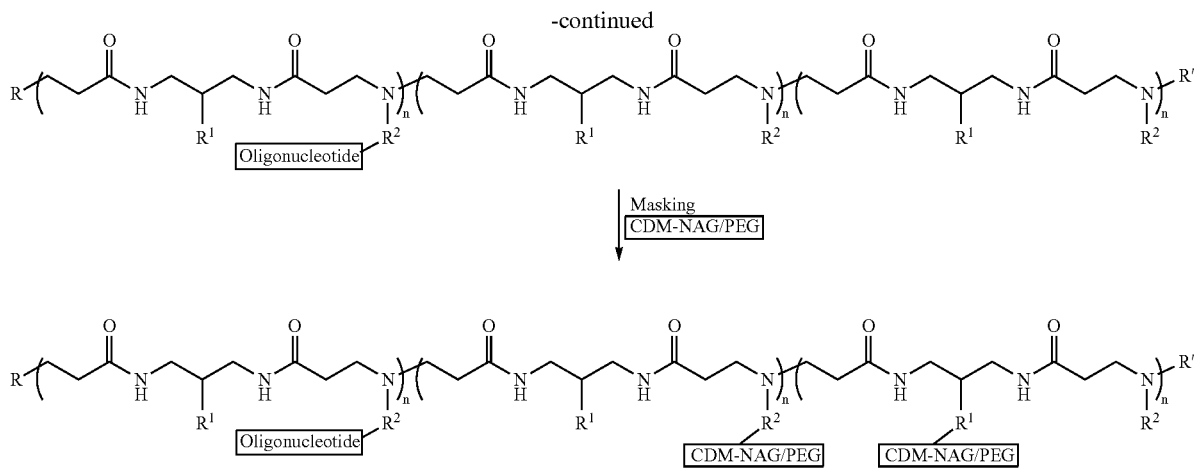

Specific Polymer Conjugation (Scheme 4)

The polymers comprising Formula Z or Z' and the specific examples shown above were synthesized for use in the following conjugation steps to ultimately create the polyconjugates of the instant invention. The polymers comprising Formula Z or Z' and the specific examples disclosed are useful in the preparation of polyconjugates which are, in turn, useful for the delivery of oligonucleotides, specifically the delivery of siRNA. Other methods for the synthesis of polyconjugates are described in WO2008/022309.

Activation of Polymer and Incorporation of siRNA (Functionalization)

About 2.6 mg of polymer in a 4 mL vial is added with ~87 µL of 100 mM TRIS, 5% glucose pH 9 buffer and stirred until the polymer is dissolved. To this solution was added 3.9 µL of (4-succinimidyloxycarbonyl-⟨-methyl-⟨-[2-pyridyldithio] toluene) solution (1 mg/100 µl in DMSO) corresponding to 1.5 wt % with respect to the polymer weight.

5'-C6-amine modified siRNA (1 g, 0.0714 mmol) is dissolved in 0.1M sodium bicarbonate buffer (20 ml, 50 mg/mL) in a vial with magnetic stir bar and cooled to 0-5° C. in an ice water bath. In a separate vial N-Succinimidyl-S-acetylthioacetate (SATA) (83 mg, 0.357 mmol, 5 equivalents) is dissolved in 0.78 ml DMSO. The SATA solution is added over 1 min and the clear, colorless reaction mixture stirred at 0-5° C. for 2 h. After 2 h, the reaction mixture is sampled and analyzed by UPLC or HPLC for completion of the conjugation. If >5% siRNA remains unreacted, another charge of SATA in DMSO (2.0 equivalents) is added and the reaction aged at 0-5° C. for completion of the SATA conjugation (confirmation by HPLC or UPLC). When there is <5% unreacted siRNA remaining by UPLC or HPLC, the reaction mixture is purified by TFF dialysis using water (~2 L) or PD10 column to remove any remaining SATA/succinimides. The recovered purified solution is lyophilized to a white fluffy solid. The recovery is typically around 95% and the purity is greater than 70% by UPLC.

Polymer-siRNA Conjugation

The activated polymer is diluted with 100 mM TRIS 5% glucose buffer pH 9 resulting in a final polymer concentration of ~2.4 mg/mL. About 0.4 mg of siRNA is added to the acvitated polymer solution and stirred at room temperature for one hour and preceded to final masking step. As shown in FIGS. 2, 3 and 4 polyconjugates have polymer siRNA conjugation efficiency >85%.

Masking of Polymer Conjugate

In a vial, 0.4 mg of CDM-PEG is weighed and 0.775 mg of CDM-NAG is added to this. The siRNA-polymer conjugate solution is then transferred into this vial containing CDM-PEG and CDM-NAG and stirred for 1 hr at room temperature. Measured masking efficiency of polyconjugates is shown in FIGS. 2, 3 and 4.

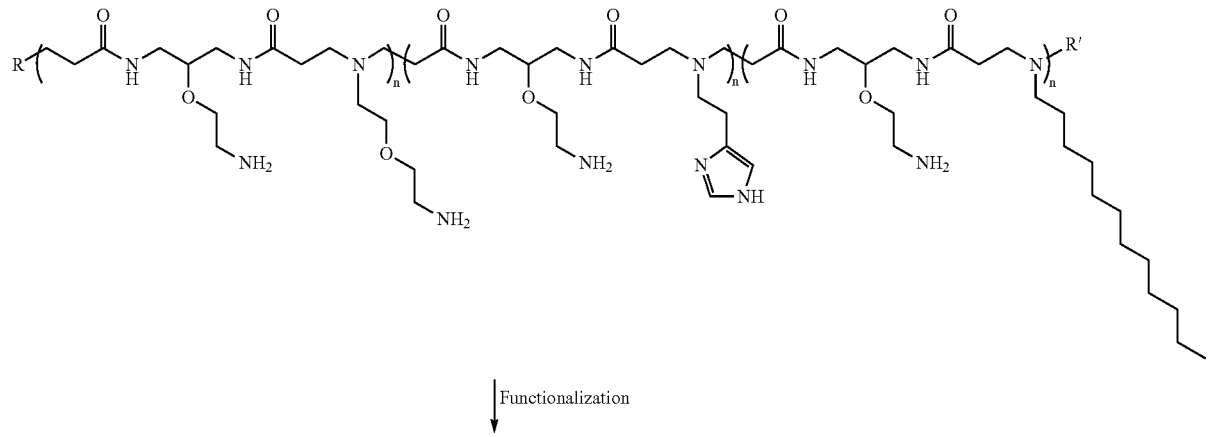

Functionalization 21 22
-continued
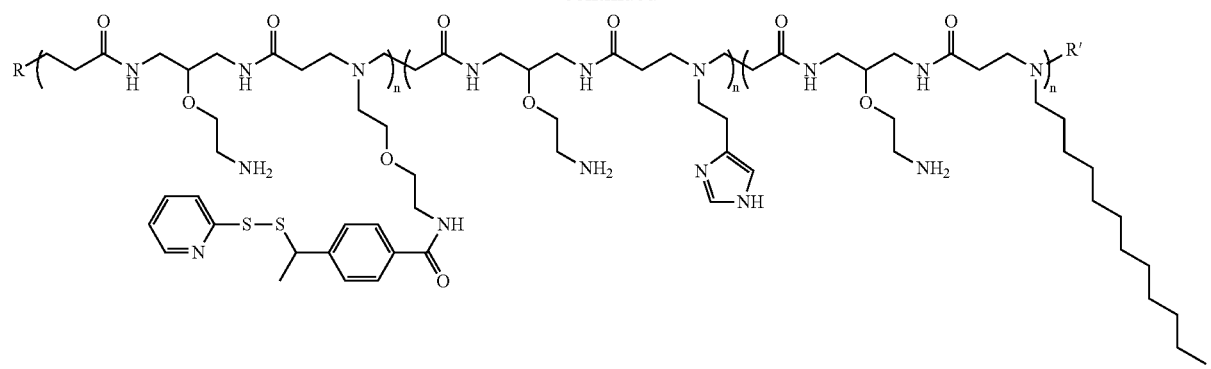
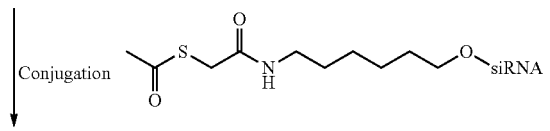
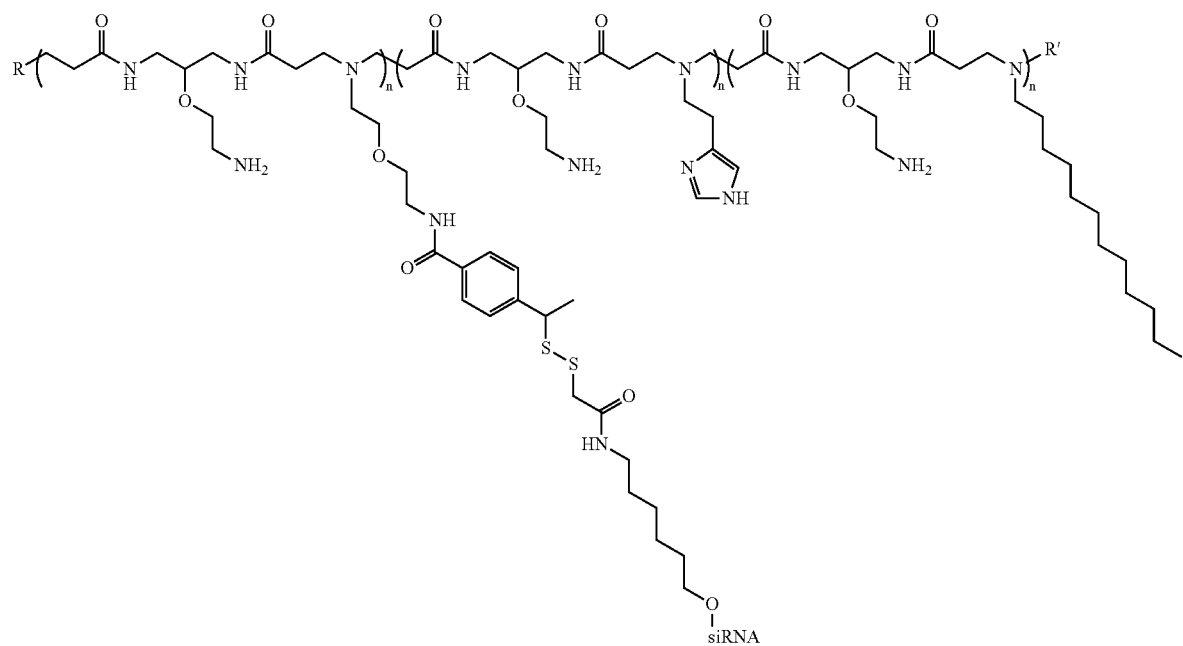
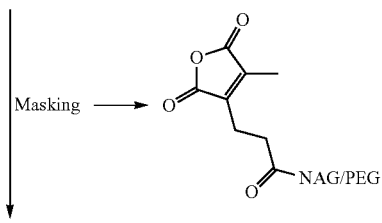

-continued

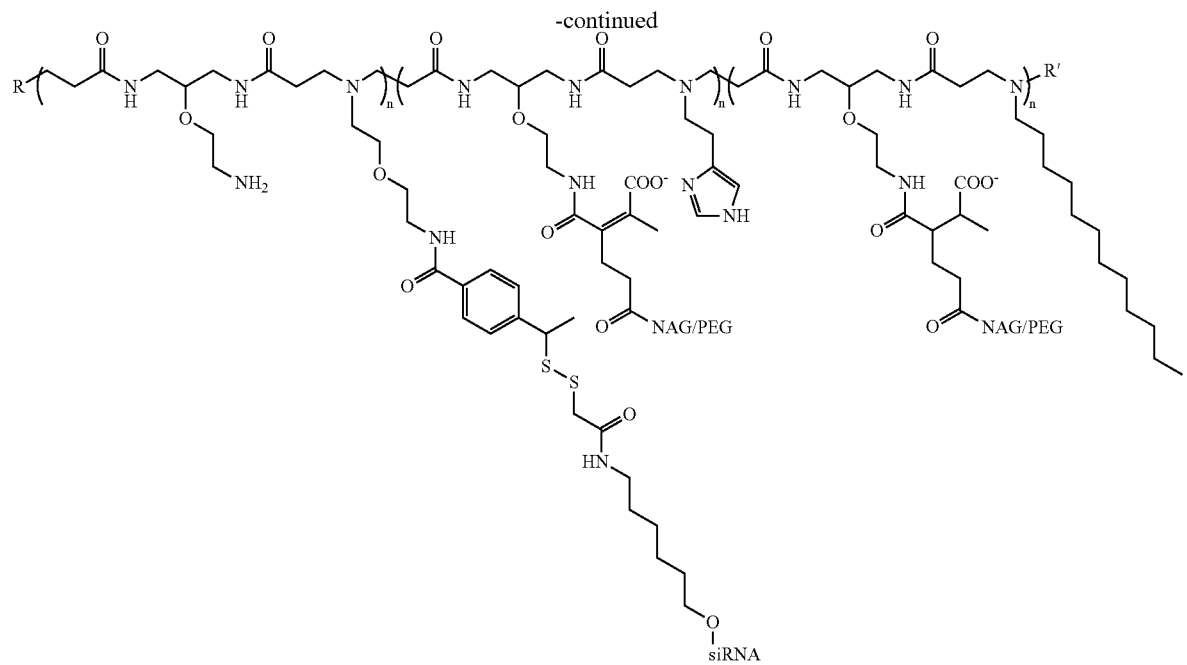

wherein the polymerconjugate is random or block and wherein n is independently 0 to 60; R is $C_4H_{10}N$; and R' is hydrogen.

As a polymer is random, siRNA can conjugate any pendent primary amine and CDM's can mask any primary amine, for example n is independently 1 to 60 and Table 2 demonstrates substituents in the identified % ratios, wherein the ratios are +/−5%.

wherein the polymerconjugate is random or block and wherein n is independently 0 to 60; R is $C_4H_{10}N$; and R' is hydrogen.

Table 2 demonstrates specific random or block polymerconjugates. In Table 2, aminoethoxy is always designated as 100, which means that aminoethoxy is present in each repeating unit of the polymerconjugate. 2-(2-aminoethoxy)ethyl-, 2-(1H-imidazol-4-yl)ethyl-, and dodecyl-containing repeating units are randomly distributed and incorporated in the identified % ratios, wherein the ratios are +/−5%.

Polyconjugates

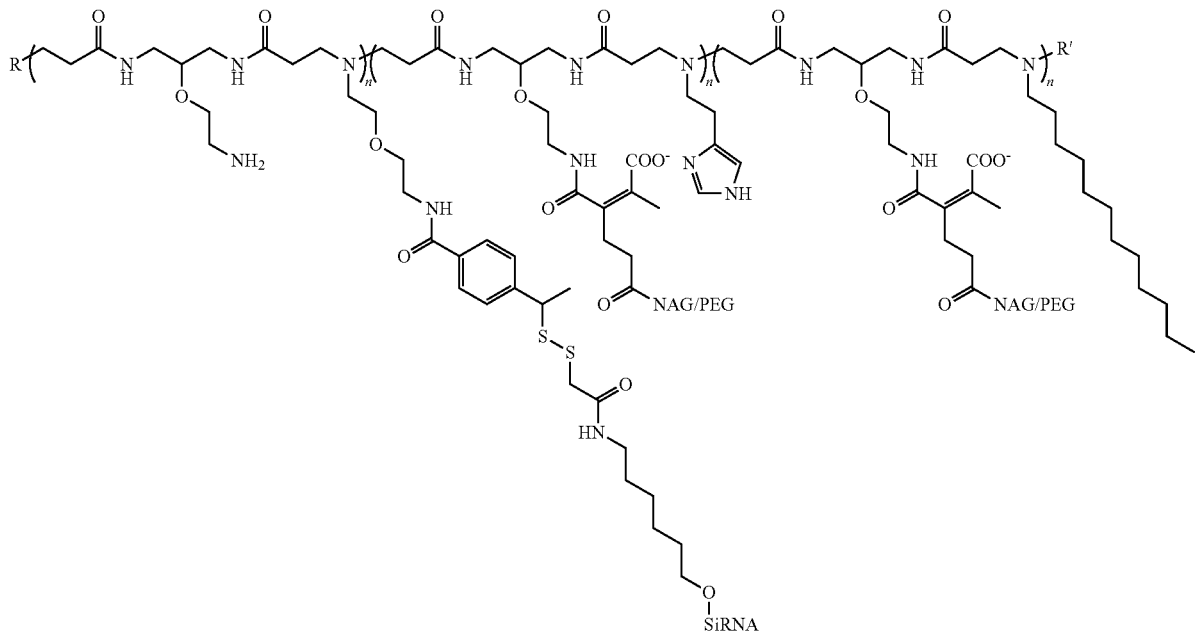

TABLE 2

| | aminoethoxy | 2-(2-aminoethoxy)ethyl | 2-(1H-imidazol-4-yl)ethyl | dodecyl |
|---|---|---|---|---|
| Polyconjugate 1 | 100 | 40 | 30 | 30 |
| Polyconjugate 2 | 100 | 30 | 50 | 20 |
| Polyconjugate 3 | 100 | 30 | 20 | 50 |
| Polyconjugate 4 | 100 | 0 | 20 | 80 |
| Polyconjugate 5 | 100 | 70 | 0 | 30 |
| Polyconjugate 6 | 100 | 20 | 80 | 0 |
| Polyconjugate 7 | 100 | 40 | 60 | 0 |

EXAMPLE 1

RBC Hemolysis Assay:

Human blood was collected in 10 ml EDTA Vacutainer tubes. A small aliquot was assessed for evidence of hemolysis by centrifugation at 15000 RCF for 2 min and non-hemolyzed samples were carried forward into the assay. Red blood cells (RBCs) were washed three times in either 150 mM NaCl/20 mM MES, pH 5.4, or 150 mM NaCl/20 mM HEPES, pH 7.5 by centrifuging at 1700×g for 3 min and resuspending in the same buffer to yield the initial volume. RBCs were then diluted in appropriate pH buffer to yield $10^8$ cells in suspension. A 10× stock concentration of each test agent (Polymerconjugate 1, Polymerconjugate 2) was prepared and a 10 point, 2-fold dilution was performed in appropriate pH buffers. The diluted test agents were added to the RBCs in appropriate pH buffers in Costar 3368 flat-bottom 96 well plates. Solutions were mixed 6 to 8 times and the microtiter plate was covered with a low evaporation lid and incubated in a 37° C. warm room or incubator for 30 minutes to induce hemolysis. The plate was then centrifuged at 1700×g for 5 min and 150 µl supernatants were transferred to a Costar 3632 clear bottom 96 well plate. Hemoglobin absorbance was read at 541 nM using a Tecan Safire plate reader and percent hemolysis was calculated assuming 100% lysis to be measured by the hemoglobin released by RBCs in 1% Triton X-100.

As shown in FIG. 1, polymerconjugates masked with acid labile masking agents at pH 7.4 don't show any lytic activity, however, become lytic at pH 5.4.

EXAMPLE 2

HepG2 Gene Silencing and Toxicity Data:

HepG2 cells were plated in 96-well microtiter plates at 6000 cells/well and incubated overnight at 37° C. to allow cell adherence. 10× stock of PCs (polyconjugates) were prepared in media and 20 µl 10× PC was added to 180 µl media already in wells resulting in 1× final treatment and a 300-0 nM 10-point half log titration, based on siRNA concentration. Cells were incubated with PCs in 37 degrees $CO_2$ incubator for 24-72 h. MTS Toxicity Assay was performed on 24 h-72 h treated cells and cytotoxicity was assessed by CellTiter 96 Aqueous One Solution Cell Proliferation Assay (Promega #G3581, Madison, Wis.). 40 µl MTS Solution was added, incubated in 37 degrees $CO_2$ incubator 1 hour, absorbance at 490 nm was read on Tecan Safire. Cells were then washed 3× in PBS and 150 µl/well bDNA DLM Lysis Buffer (Panomics "Quantigene" 1.0 bDNA kit #QG0002, Fremont, Calif.) was added. Plate was then incubated at 37 degrees in Warm Room 30 min. Lysates were removed and frozen at −70 degrees C. overnight. The next day, all cell lysates were thawed at RT and 20 µl of each lysate was removed and used for determination of total protein using Micro BCA Protein Assay kit (Pierce #23235, through Thermo Scientific, Rockford, Ill.). Absorbance was measured on Tecan Safire: Wavelength=562 nM, Plate=Costar96 ft, Number of Reads=100, Time between Reads=5.50 µl each lysate was also used to determine mRNA expression levels in cells treated with SSB siRNA.

ApoB mRNA knockdown was determined using Quantigene 1.0 bDNA Assay (Panomics # QG0002 Lot # 51CW36, Fremont, Calif.), a kit designed to quantitate RNA using a set of target-specific oligonucleotide probes.

Active siRNA 1: Zimmerman Apo B:

Zimmermann et al., (2006) Nature, 441(7089):111-114 or doi:10.038/nature04688 (see supplementary information).

Active siRNA 2: Sci 10 Apo B:

```
Sci10 ApoB siRNA
                                  (SEQ ID NO.: 1)
5'-iB-CUUUAACAAUUCCUGAAAUTsT-iB-3'

(SEQ ID NO.: 2)
    3'-UsUGAAAUUGUUAAGGACUsUsUsA-5'
```

U - Ribose
iB - Inverted deoxy abasic
AGU - 2' Fluoro
T - 2' Deoxy
CU - 2' $OCH_3$
s - phophorothioate linkage The passenger strand contains a primary amine with six carbon linker at 5' end, which is used to conjugate the siRNA to the polymer.

Control siRNA: Low Hex 9:

```
Low Hex 9 siRNA
                                  (SEQ ID NO.: 3)
5'-amil-iB-CUAGCUGGACACGUCGAUATsT-iB-3'

(SEQ ID NO.: 4)
    3'-UsUGAUCGACCUGUGCAGCUAU-5'
``` amil - amino linker
iB - Inverted deoxy abasic
CU - 2'-Fluoro (F)
AGT - 2'-Deoxy
UGA - 2'-Methoxy (OMe)
AU - Ribose
s - phosphorothioate linkage The passenger strand contains a primary amine with six carbon linker at 5' end, which is used to conjugate the siRNA to the polymer.

Panomics Quantigene bDNA Kit # QG0002-Protocol for 96 Well Plate:

Day 1

Make diluted lysis mixture (DLM) by mixing 1 volume of lysis mixture with 2 volumes of Nuclease Free water (Ambion cat # AM9930). Aspirate (PBS) from plate. Add 150 µl DLM to each well and mix. (Include Column 1 as Buffer Alone Background). Incubate at 37° C. for 30 minutes. (After heating, Lysates can be placed in the −70° C. freezer until analysis is performed. If lysates are frozen, thaw at Room Temperature and incubate at 37° C. for 30 minutes and mix well before adding the samples to the capture plate.) Bring all reagents to Room Temperature before use, including the capture plates. Dilute CE, LE and BL probe set components: 0.1 µl well each into DLM. Add (100-X) µl diluted probe set/well. Add (X) µl cell lysate/well. Cover with foil plate sealer.

Incubate at 53° C. for 16-20 hrs. Note: If assay contains multiple plates, perform steps 7, 8, 9 on 2-3 plates at a time and place at 53° C. before going on to next 2-3 plates.

Day 2

Bring Amplifier, Label Probe and Substrate to Room Temperature. Vortex and briefly centrifuge the tubes of Amplifier and Label Probe to bring the contents to the bottom of the tube. Prepare Wash buffer: add 3 ml Component 1 and 5 ml Component 2 to 1 L distilled water. (Wash Buffer is stable at Room Temperature for up to 6 months)

Prepare as needed: Amplifier Working solution, Label Probe Working Solution, and Substrate Working Solution:

Amplifier Working Solution—1:1000 dilution into Amplifier/Label Probe diluent.

Label Probe Working solution—1:1000 dilution into Amplifier/Label Probe diluent.

Substrate Working Solution—1:333 dilution of 10% Lithium Lauryl Sulfate Substrate into Substrate Solution (protect from light).

Add 200 μl/well of wash buffer to overnight hybridization mixture. Repeat washes 3× with 300 μl of Wash Buffer. *Do not let the capture plates stand dry for longer than 5 minutes. Add 100 μl/well of Amplifier Working Solution. Seal plate with clear seal and incubate at 53° C. for 30 minutes. Wash plate 3× with 300 μl of Wash Buffer. Add 100 μl well of Label Probe Working Solution. Seal plate with clear seal and incubate at 53° C. for 30 minutes. Wash plate 3× with 300 μl of Wash Buffer. Add 100 μl/well Substrate Working Solution. Seal plate with foil seal and incubate at 53° C. for 15 minutes. Let plate stand at Room Temperature for 10 minutes. Read in luminometer with integration time set to 0.2 seconds. bDNA data was normalized to protein and graphed using GraphPad Prism Program using non-linear regression curve fit analysis.

As shown in Table 3, all the polyconjugates are active in vitro.

TABLE 3

|  | bDNA (nM) | MTS (nM) |
| --- | --- | --- |
| Polyconjugate 1 | 126 | >300 |
| Polyconjugate 2 | 112 | >300 |
| Polyconjugate 3 | 135 | >300 |
| Polyconjugate 4 | 11 | 13 |
| Polyconjugate 5 | 148 | >300 |
| Polyconjugate 6 | 53 | >300 |
| Polyconjugate 7 | 59 | >300 |

In Vivo Evaluation of Efficacy (Mice):

CD1 mice were tail vein injected with the siRNA containing polymer conjugates at a dose of 3 mg/kg in a volume of 0.2 mL, 100 mM TRIS/9% glucose, pH9, vehicle. Five days post dose, mice were sacrificed and liver tissue samples were immediately preserved in RNALater (Ambion). Preserved liver tissue was homogenized and total RNA isolated using a Qiagen bead mill and the Qiagen miRNA-Easy RNA isolation kit following the manufacturer's instructions. Liver ApoB mRNA levels were determined by quantitative RT-PCR. Message was amplified from purified RNA utilizing primers against the mouse ApoB mRNA (Applied Biosystems Cat. No. Mm01545156_m1). The PCR reaction was run on an ABI 7500 instrument with a 96-well Fast Block. The ApoB mRNA level is normalized to the housekeeping PPIB mRNA and GAPDH. PPIB and GAPDH mRNA levels were determined by RT-PCR using a commercial probe set (Applied Biosytems Cat. No. Mm00478295_m1 and Mm4352339E_m1). Results are expressed as a ratio of ApoB mRNA/PPIB/GAPDH mRNA. All mRNA data is expressed relative to the vehicle control.

As shown in FIG. 2, mice treated with active Apo B siRNA polyconjugates show significant reduction in mRNA expression, whereas no reduction in mRNA expression was observed with control siRNA polyconjugates.

Polymer driven knockdown (KD) was observed with polymerconjugate 1 as shown in FIG. 2: ID-B and ID-E. The amount of polymer used in both cases is the same while the siRNA doses are different (24 & 3 mpk for E and 24 & 6 mpk for B). Both of these conjugates gave same KD.

Dose depended KD was observed with polyconjugate 1 and 2 at 6, 3 and 1 mpk dose.

As shown in FIG. 3, all the polyconjugates (3, 4, 5, 6 and 7) are active in vivo and the percentage of KD varies with the change in incorporation ratios of monomers.

In Vivo Evaluation of Efficacy (Rats)

Polyconjugates were dosed by tail vein injection into female Sprague Dawley rats (150-200 grams) at a rate of 3 ml/min. Five days post dose, rats were sacrificed and liver tissue samples were immediately preserved in RNALater (Ambion). Preserved liver tissue was homogenized and total RNA isolated using a Qiagen bead mill and the Qiagen miRNA-Easy RNA isolation kit following the manufacturer's instructions. Liver ApoB mRNA levels were determined by quantitative RT-PCR. Message was amplified from purified RNA utilizing primers against the mouse ApoB mRNA (Applied Biosystems Cat. No. Mm01545156_m1). The PCR reaction was run on an ABI 7500 instrument with a 96-well Fast Block. The ApoB mRNA level is normalized to the housekeeping PPIB mRNA and GAPDH. PPIB and GAPDH mRNA levels were determined by RT-PCR using a commercial probe set (Applied Biosytems Cat. No. Mm00478295_m1 and Mm4352339E_m1). Results are expressed as a ratio of ApoB mRNA/PPIB/GAPDH mRNA. All mRNA data is expressed relative to the vehicle control. Alanine aminotransferanse (ALT) was measured using the ADVIA Chemistry Systems Alanine Aminotransferase (ALT) method, 03815151, Rev. A., according to the following reference, Clinical and Laboratory Standards Institute. *Laboratory Documents: Development and Control; Approved Guideline—Fifth Edition*. CLSI document GP2-A5 [ISBN 1-56238-600-X]. Clinical and Laboratory Standards Institute, 940 West Valley Road, Suite 1400, Wayne, Pa., 19807-1898 USA, 2006.

As shown in FIG. 4, dose depended KD was observed with polyconjugate 2 at 6, 3 and 1 mpk dose in rats with 2 times elevation in ALT.

What is claimed is:

1. A polymer comprising Formula Z:

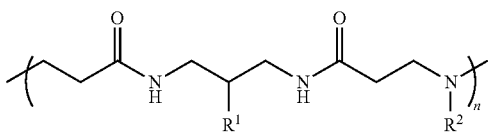

wherein:
n is 2 to 250;
R¹ is independently selected from the group consisting of a primary amine, secondary amine, tertiary amine, and quaternary amine; and
R² is independently selected from the group consisting of a primary amine, secondary amine, tertiary amine, quaternary amine, a heterocyclic amine, and a lipophilic group;

or stereoisomer thereof.

2. A polymer according to claim 1 comprising Formula Z':

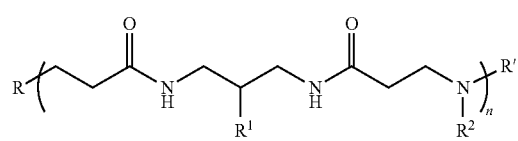

wherein:
n is 2 to 250;
R is a capped end group selected from the group consisting of a primary amine and secondary amine;
R' is hydrogen or methylene;
R¹ is independently selected from the group consisting of a primary amine, secondary amine, tertiary amine, and quaternary amine; and
R² is independently selected from the group consisting of a primary amine, secondary amine, tertiary amine, quaternary amine, a heterocyclic amine, and a lipophilic group;

or stereoisomer thereof.

3. A polymer according to claim 1 comprising Formula Z', wherein:
n is 2 to 250;
R is $C_4H_{10}N$;
R' is hydrogen;
R¹ is aminoethoxy; and
R² is independently selected from dodecyl, 2-(1H-imidazol-4-yl)ethyl and 2-(2-aminoethoxy)ethyl;

or stereoisomer thereof.

4. A polymer according to claim 1 which is selected from:

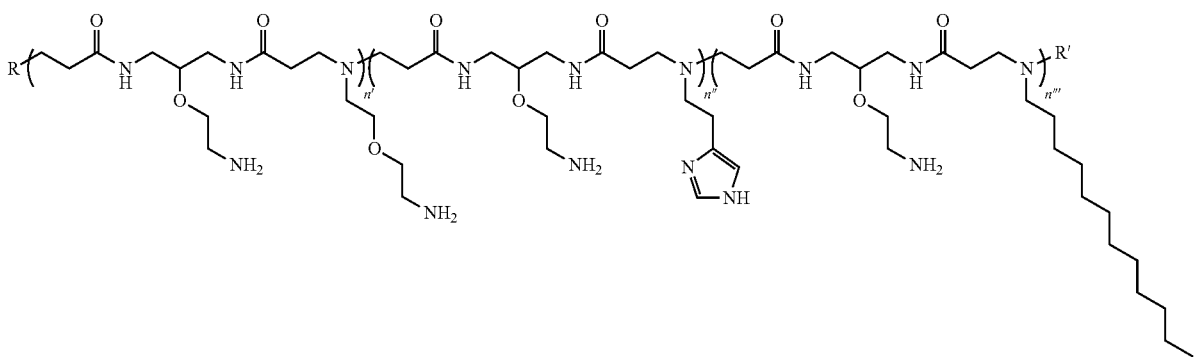

wherein the polymer is random or block and wherein n', n", and n'" are independently 0 to 60, provided that the sum of n', n", and n'" is at least 2; R is $C_4H_{10}N$; and R' is hydrogen.

5. A polymer conjugate composition comprising a polymer according to claim 1 of Formula Z, a linker and an oligonucleotide.

6. A polymer conjugate composition of claim 5 further comprising a masking agent.

7. A polymer conjugate composion of claim 5 further comprising a targeting ligand.

8. A polymer conjugate composition of claim 5 further comprising a masking agent and a targeting ligand.

9. A polymer conjugate composition made by the
1) synthesis of an activated polymer comprising Formula Z:

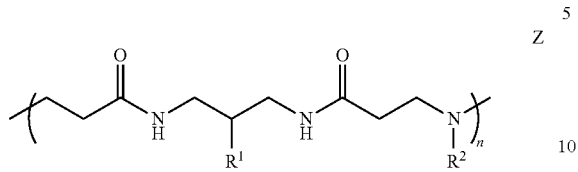

wherein:
  n is 2 to 250;
  $R^1$ is independently selected from the group consisting of a primary amine, secondary amine, tertiary amine, and quaternary amine; and
  $R^2$ is independently selected from a primary amine, secondary amine, tertiary amine, quaternary amine, a heterocyclic amine, and a lipophilic group;
or stereoisomer thereof;
  2) synthesis of an activated oligonucleotide; and
  3) conjugation of the activated polymer with the activated oligonucleotide;
  optionally including the addition of a masking agent and/or a targeting ligand.

* * * * *